(12) United States Patent  (10) Patent No.: US 8,126,205 B2
Levenson et al.  (45) Date of Patent: Feb. 28, 2012

(54) SAMPLE IMAGING AND CLASSIFICATION

(75) Inventors: Richard Levenson, Brighton, MA (US);
Clifford C. Hoyt, Wellesley, MA (US)

(73) Assignee: Cambridge Research & Instrumentation, Inc., Woburn, MA (US)

( * ) Notice: Subject to any disclaimer, the term of this patent is extended or adjusted under 35 U.S.C. 154(b) by 1098 days.

(21) Appl. No.: 11/861,060

(22) Filed: Sep. 25, 2007

(65) Prior Publication Data
US 2008/0074644 A1 Mar. 27, 2008

Related U.S. Application Data

(60) Provisional application No. 60/972,508, filed on Sep. 14, 2007, provisional application No. 60/847,300, filed on Sep. 25, 2006.

(51) Int. Cl.
*G06K 9/00* (2006.01)
(52) U.S. Cl. ........................................ 382/103
(58) Field of Classification Search .................. None
See application file for complete search history.

(56) References Cited

U.S. PATENT DOCUMENTS

| 5,065,763 A * | 11/1991 | Green et al. ............. 600/453 |
| 5,241,362 A | 8/1993 | Ukon et al. |
| 5,521,705 A | 5/1996 | Oldenbourg et al. |
| 5,539,517 A | 7/1996 | Cabib et al. |
| 5,661,557 A | 8/1997 | Da Silva et al. |
| 5,784,162 A | 7/1998 | Cabib et al. |
| 5,991,028 A | 11/1999 | Cabib et al. |
| 5,995,645 A | 11/1999 | Soenkson et al. |
| 6,007,996 A | 12/1999 | McNamara et al. |
| 6,069,690 A | 5/2000 | Xu et al. |
| 6,142,629 A | 11/2000 | Adel et al. |
| 6,178,257 B1 | 1/2001 | Alumot et al. |
| 6,373,568 B1 | 4/2002 | Miller et al. |
| 6,396,053 B1 | 5/2002 | Yokoi |
| 6,421,131 B1 | 7/2002 | Miller |
| 6,466,687 B1 | 10/2002 | Uppaluri et al. |
| 6,690,466 B2 | 2/2004 | Miller et al. |
| 6,825,921 B1 | 11/2004 | Modlin et al. |
| 6,920,239 B2 | 7/2005 | Douglass et al. |
| 6,924,893 B2 | 8/2005 | Oldenbourg et al. |
| 7,123,360 B2 | 10/2006 | Treado et al. |
| 7,374,907 B1 | 5/2008 | Voneiff et al. |
| 7,418,169 B2 | 8/2008 | Tearney et al. |
| 7,831,106 B2 | 11/2010 | Elsner et al. |
| 2001/0052979 A1 | 12/2001 | Treado et al. |

(Continued)

FOREIGN PATENT DOCUMENTS

WO    WO 98/43042    10/1998

(Continued)

OTHER PUBLICATIONS

Pickering J.G. et al., "Fibrosis in the transplanted heart and its relation to donor ischemic time. Assessment with polarized light microscopy and digital image analysis", Circulation, vol. 1(3): 949-958 (1990).*

(Continued)

*Primary Examiner* — Brian Werner
*Assistant Examiner* — Nirav G Patel
(74) *Attorney, Agent, or Firm* — Fish & Richardson P.C.

(57) ABSTRACT

Disclosed herein are methods and apparatus for obtaining at least one absorption image and at least one birefringence image of a stained sample.

24 Claims, 11 Drawing Sheets

U.S. PATENT DOCUMENTS

| | | | |
|---|---|---|---|
| 2002/0093648 | A1 | 7/2002 | Nikoonahad et al. |
| 2002/0107650 | A1 | 8/2002 | Wack et al. |
| 2002/0109110 | A1 | 8/2002 | Some et al. |
| 2003/0138140 | A1 | 7/2003 | Marcelpoil et al. |
| 2003/0223248 | A1 | 12/2003 | Cronin et al. |
| 2004/0052730 | A1 | 3/2004 | Hochman |
| 2004/0081204 | A1 | 4/2004 | Burnett |
| 2004/0192645 | A1 | 9/2004 | Hollingsworth et al. |
| 2005/0065440 | A1 | 3/2005 | Levenson |
| 2006/0019409 | A1 | 1/2006 | Nelson et al. |
| 2006/0082762 | A1 | 4/2006 | Leverette et al. |
| 2006/0159664 | A1 | 7/2006 | Pandit et al. |
| 2006/0170907 | A1 | 8/2006 | Tuschel |
| 2006/0245631 | A1* | 11/2006 | Levenson et al. ............ 382/133 |
| 2007/0016082 | A1 | 1/2007 | Levenson et al. |
| 2007/0103693 | A1 | 5/2007 | Everett et al. |
| 2007/0231784 | A1* | 10/2007 | Hoyt et al. ........................ 435/4 |
| 2008/0074644 | A1 | 3/2008 | Levenson et al. |
| 2009/0117040 | A1 | 5/2009 | Wanker et al. |

FOREIGN PATENT DOCUMENTS

| | | |
|---|---|---|
| WO | WO 99/58939 | 11/1999 |
| WO | WO 2005/040769 | 5/2005 |
| WO | WO 2006/081547 | 8/2006 |
| WO | WO 2006/081547 A | 8/2006 |
| WO | WO 2008/039758 | 4/2008 |

OTHER PUBLICATIONS

Jin, L.-W.; Claborn, K. A.; Kurimoto, M.; Geday, M. A.; Maezawa, I.; Sohraby, F.; Estrada, M.; Kaminsky, W.; Kahr, B."Imaging linear biregringence and dichroism in cerebral amyloid pathologies," Proc. Natl. Acad. Sci. U.S.A. 2003, 100, 15294-15298.*

C.M. Bishop et al., "The Multi-Layer Perceptron," Neural Networks for Pattern Recognition (Oxford University Press, 1995), pp. 116-163.

Cory Pelletier et al., "Noninvasive polarized light microscopy quantitatively distinguishes the multilaminar structure of the zona pellucida of living human eggs and embryos," Fertility and Sterility 81 Suppl. 1: 850-856 (2004).

D. Keefe et al., "Imaging meiotic spindles by polarization light microscopy: principles and applications to IVF," Reproductive BioMedicine 7: 24-29 (2003).

L. Jimenez et al., "Hyperspectral Data Analysis and Feature Reduction via Projection in Pursuit," IEEE Transactions on Geoscience and Remote Sensing 37(6): 2653-2667 (1999).

L. Jimenez et al., "Supervised Classification in High Dimensional Space: Geometrical, Statistical and Asymptotical Properties of Multivariate Data," IEEE Transations on Geoscience and Remote Sensing 37(6): 1-32 (1999).

L.O. Jimenez et al., "High Dimensional Feature Reduction via Projection Pursuit," TR-ECE 96-5, School of Engineering, Purdue University (Apr. 1995).

R. Oldenbourg, "A new view on polarization microscopy," Nature 381: 811-812 (1996).

R. Oldenbourg, "Polarized Light Microscopy of Spindles," Methods in Cell Biology 61: 175-208 (1999).

R.M. Haralick et al., "Textural features for image classification," IEEE Transactions on Systems, Man and Cybernetics, vol. SMC-3: 610-621 (1973).

S. Aksoy et al., "Textural Features for Image Database Retrieval," IEEE Proceedings of the Workshop on Content-Based Access of Image and Video Libraries, pp. 45-49 (1998).

Katalin et al., "Combination of digital image analysis and polarization microscopy: theoretical considerations and experimental data", Microscopy Research and Technique, vol. 43: 511-517 (1998).

Zhang et al., "Quantitative analysis of fibrosis formation on the microcapsule surface with the use of picro-sirius red staining, polarized light microscopy, and digital image analysis", Journal of Biological Materials Research, vol. 76(1): 120-125 (2006).

International Search Report for PCT/US2007/079397, Mar. 25, 2009.

K.P. Camilleri et al., "Spectral Unmixing of Mixed Pixels for Texture Boundary Refinement," IEEE Proceedings of the 15th International Conference on Pattern Recognition, pp. 1084-1087 (2000).

W.-H. Wang et al., "The spindle observation and its relationship with fertilization after intracytoplasmic sperm injection in living human oocytes," Fertility and Sterility 75(2): 348-353 (2001).

J.F. de Boer et al., "Two-dimensional birefringence imaging in biological tissue by polarization-sensitive optical coherence tomography," Optics Letters 22(12): 934-936 (1997).

Office Action in U.S. Appl. No. 11/861,057, dated Mar. 8, 2011.

Written Opinion of the International Searching Authority for International Application No. PCT/US2007/079397, Aug. 7, 2008.

* cited by examiner

SAMPLE IMAGING AND CLASSIFICATION

CROSS-REFERENCE TO RELATED APPLICATIONS

This application claims priority to the following applications: U.S. Provisional Patent Application Ser. No. 60/847,300, filed on Sep. 25, 2006; and U.S. Provisional Patent Application Ser. No. 60/972,508, filed on Sep. 14, 2007. The entire contents of each of the foregoing applications are incorporated herein by reference.

TECHNICAL FIELD

This disclosure relates to imaging and classifying samples, e.g., microscope imaging of tissue samples.

BACKGROUND

Personalized medicine promises to revolutionize clinical care by providing more accurate diagnoses, better targeted therapies, and response monitoring. Approaches to personalized medicine can benefit from determining which particular disease configuration a patient has through the application of one or more stains to a tissue sample taken from the patient, and subsequent assessment of the stained tissue sample.

Biological stains are generally used in tissue histology and other fields to enhance contrast between particular structures of interest in tissues and the remainder of a tissue section. Such contrast is typically observed when stained tissue samples are viewed under an optical microscope. Certain immunohistochemical (IHC) stains bind selectively to certain structures and/or cell types within a tissue sample. Under a microscope, the color of regions that include stain molecules bound to tissue structures can be different from the color of unstained regions of the sample. The resulting color contrast can allow a trained operator to make a visual assessment of the sample.

Anatomical and surgical pathology rely heavily on visual assessment of stained clinical tissue sections. Commonly used stains such as hematoxylin and eosin (H&E) achieve specificity according to the manner in which the stain interacts with components of tissue sections. For example, stains can be applied to selectively stain disease-related proteins and other components in tissue sections. These stains reveal disease-specific architectures and morphologies which provide cues for visual diagnosis.

Fibrosis results from wound-healing responses to chronic tissue injury in a variety of tissues. For example, renal fibrosis is a progressive process that can lead to end-stage renal failure, which may require dialysis and/or kidney transplantation. Liver fibrosis can result in cirrhosis, portal hypertension, and liver failure, and may require liver transplantation. The assessment of the severity of old and/or active fibrotic processes in subjects is important in diagnosing a variety of fibrosis-related conditions, and in evaluating subject responses to antifibrotic therapy.

Fibrosis is characterized by excessive accumulation of extracellular matrix constituents including collagens, proteoglycans, and glycoproteins. One method for assessment of fibrosis activity is by examining tissue sections (e.g., liver biopsy sections) for the presence of collagen under an optical microscope. However, common general purpose histological stains such as H&E do not provide reliable quantitative information about collagen accumulation under typical assessment conditions. Instead, special stains such as Masson's trichrome stain and picosirius red are typically used to measure fibrosis stage in tissue sections.

Picosirius red is birefringent and collagen-specific, and chemically enhances the birefringence of collagen fibers when it binds to the fibers. Bound picosirius red can increase the birefringence of collagen fibers so that relative amounts or types of collagen can be discerned as colors under a conventional white light polarized light microscope with crossed circular polarizers and broadband illumination (e.g., several hundreds of nanometers). For example, larger collagen fibers may appear bright yellow or orange, while smaller fibers may appear green.

Examination of tissue sections typically begins with a pathologist performing a visual assessment of an H&E-stained sample, and deciding that further assessment with a special stain is needed. Another sample is then stained with trichrome (which demarks collagen with a blue color to aid in visual assessment), or occasionally with picosirius red, and viewed under a polarized light microscope equipped with crossed circular polarizers. One of the polarizers can be slightly detuned so that the microscope's background image field is not completely dark. Images of the second sample are recorded, and collagen identified in the second sample can be qualitatively categorized based on visual inspection of its color in the images.

SUMMARY

In general, in a first aspect, the disclosure features a method that includes obtaining at least one absorption image and at least one birefringence image of a stained sample.

Embodiments of the method can include one or more of the following features.

The method can include combining information derived from the at least one absorption image and information derived from the at least one birefringence image, and assessing a disease condition in the stained sample based on the combined information. Assessing a disease condition can include assessing a type or a stage of fibrosis in the sample.

The method can include identifying the presence of collagen in the sample based on the at least one birefringence image. The method can include assessing a disease condition in the sample based on the identified collagen. The at least one absorption image can be obtained by measuring light absorption by one or more stains in the sample that are not specific for collagen. The measured light absorption may not arise from absorption of incident light by a trichrome stain, picosirius red, or Congo red.

The at least one absorption image can be obtained by directing light having a central wavelength that corresponds to a first wavelength to be incident on the sample, the at least one birefringence image is obtained by directing light having a central wavelength that corresponds to a second wavelength to be incident on the sample, and a difference between the first and second wavelengths is 5 nm or less.

The at least one absorption image can be obtained by directing light having a central wavelength that corresponds to a first wavelength to be incident on the sample, the at least one birefringence image is obtained by directing light having a central wavelength that corresponds to a second wavelength to be incident on the sample, and a difference between the first and second wavelengths is 50 nm or more.

The sample can include at least one fluorescent stain.

The combined information can be represented as an image stack, where at least one plane of the image stack includes information derived from an absorption image of the sample and at least one plane of the image stack includes information derived from a birefringence image of the sample.

The method can include combining information derived from the at least one absorption image and information derived from the at least one birefringence image to form a composite image, and displaying the composite image to a system operator. The combining and displaying can include producing a first color image of the sample based on an absorption image, producing a second color image of the sample based on a birefringence image, and overlaying the first and second color images to produce the composite image.

Obtaining at least one absorption image can include obtaining two or more absorption images, where each absorption image is obtained with incident light having a different central wavelength. Obtaining at least one birefringence image can include obtaining at least two birefringence images, where at least one of the at least two birefringence images includes information about a magnitude of optical retardance in the sample and at least one of the at least two birefringence images includes direction information about optical retardance in the sample.

Identifying the presence of collagen can include identifying one or more different types of collagen in the sample. The one or more different types of collagen can be identified based on a comparison between birefringence information derived from the at least one birefringence image and a look-up table that includes birefringence information.

Embodiments of the method can also include any of the other method steps disclosed herein, as appropriate.

In another aspect, the disclosure features an apparatus that includes: (a) a microscope imaging system configured to obtain at least one absorption image and at least one birefringence image of a stained sample; and (b) an electronic processor coupled to the microscope imaging system and configured to receive information about one or more stains in the stained sample, to combine information from the at least one absorption image and the at least one birefringence image, and to identify structural entities in the sample based on at least a portion of the combined information derived from the at least one birefringence image.

Embodiments of the apparatus can include one or more of the following features.

The combined information can be represented as an image stack, where at least one plane of the image stack includes information derived from an absorption image of the sample and at least one plane of the image stack includes information derived from a birefringence image of the sample.

The electronic processor can be configured to obtain the at least one absorption image by measuring light absorption by one or more stains present in the sample that are not specific for collagen.

The structural entities can include collagen.

The processor can be configured to assess a disease condition in the sample based on the combined information.

The apparatus can include a display unit, where the processor is configured to combine information from the at least one absorption image and the at least one birefringence image to form a composite image, and where the processor is configured to display the composite image to a system operator. The processor can be configured to form the composite image by producing a first color image derived from the at least one absorption image, producing a second color image derived from the at least one birefringence image, and overlaying the first and second color images to form the composite image.

Embodiments of the apparatus can also include any of the other features disclosed herein, as appropriate.

In a further aspect, the disclosure features a method that includes identifying collagen in a stained tissue sample, where the identifying includes obtaining at least one absorption image of the sample by measuring light absorption by one or more stains in the sample that are not specific for collagen, obtaining at least one birefringence image of the sample, combining information derived from the at least one absorption image and the at least one birefringence image, and identifying collagen based on a portion of the combined information derived from the at least one birefringence image.

Embodiments of the method can include any of the method steps disclosed herein, as appropriate.

In another aspect, the disclosure features a method that includes obtaining at least one non-birefringence image and at least one birefringence image of a stained sample, and classifying regions of the stained sample into a plurality of classes based on the at least one non-birefringence image and the at least one birefringence image.

Embodiments of the method can include one or more of the following features.

The at least one non-birefringence image can include at least one absorption image. Alternatively, or in addition, the at least one non-birefringence image can include at least one fluorescence image. Alternatively, or in addition, the at least one non-birefringence image can include at least one absorption image and at least one fluorescence image.

The method can include combining information derived from the at least one non-birefringence image and the at least one birefringence image and classifying regions of the sample based on the combined information, where the combined information can be represented as an image stack, and where at least one plane of the image stack can include an image derived from a non-birefringence image of the sample and at least one plane of the image stack can include an image derived from a birefringence image of the sample.

Two or more non-birefringence images can be obtained by directing radiation to be incident on the sample and measuring radiation transmitted or reflected by the sample, where the two or more non-birefringence images each correspond to a different wavelength of incident radiation.

Two or more non-birefringence images can be obtained by directing radiation to be incident on the sample and measuring radiation emitted by the sample, where the two or more non-birefringence images each correspond to a different wavelength of emitted radiation.

The method can include decomposing at least one of the non-birefringence images into a plurality of component images, where each image of the plurality of component images corresponds substantially only to a single non-birefringence contributor. At least one image of the plurality of component images can correspond to a stain applied to the sample. Alternatively, or in addition, at least one image of the plurality of component images can correspond to a fluorescent stain or entity within the sample.

The method can include combining information derived from at least one of the component images with information derived from the at least one birefringence image, where the combined information can be represented as an image stack, and where at least one plane of the image stack can correspond to a component image.

The stained sample can include two or more stains, where each image of the plurality of component images corresponds substantially only to non-birefringence contributions from one of the two or more stains.

The stained sample can include two or more stains, where the at least one non-birefringence image includes two or more non-birefringence images, and each of the two or more non-birefringence images corresponds substantially only to spectral contributions from one of the two or more stains.

The method can include displaying classification results to a system operator, where the displaying includes displaying an image of the sample, the image including a plurality of shaded regions that correspond to classified regions of the sample.

The method can include assessing a disease condition in a patient based on the classified regions of the sample.

Embodiments of the method can also include any of the other method steps disclosed herein, as appropriate.

In a further aspect, the disclosure features an apparatus that includes: (a) a microscope imaging system configured to obtain one or more non-birefringence images and one or more birefringence images of a stained sample; and (b) an electronic processor coupled to the imaging system and configured to receive information about one or more stains in the stained sample and to classify regions of the sample into a plurality of classes based on information derived from the non-birefringence images and the birefringence images.

Embodiments of the apparatus can include one or more of the following features.

The electronic processor can be configured to decompose at least some of the one or more non-birefringence images into component images prior to the classifying. The sample can include two or more stains, where each of the component images corresponds to spectral contributions from substantially only one of the two or more stains. Alternatively, or in addition, the sample can include two or more different types of fluorescent stains or entities, where each of the component images corresponds to spectral contributions from substantially only one of the two or more different types of fluorescent stains or entities.

The apparatus can include a display unit, where the processor is configured to display results of the classification to a system operator. The displayed classification results can include an image of the sample that includes differently-shaded regions, the differently-shaded regions corresponding to different classes.

The processor can be configured to decompose at least some of the non-birefringence images into component images and to combine information derived from at least one of the component images and from the at least one birefringence image, where the combined information can be represented as an image stack, and where at least one plane of the image stack corresponds to a component image. At least one plane of the image stack can correspond to information derived from a birefringence image of the sample, where the processor is configured to classify regions of the sample based on information derived from multiple planes of the image stack.

The processor can be configured to classify the sample based on spectral information and texture information derived from the one or more non-birefringence images and the one or more birefringence images of the sample.

The processor can be configured to assess a disease condition in a subject based on the classification of the sample.

The one or more non-birefringence images of the sample can include at least one absorption image and at least one fluorescence image.

Embodiments of the apparatus can also include any of the other features disclosed herein, as appropriate.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Figure 1:
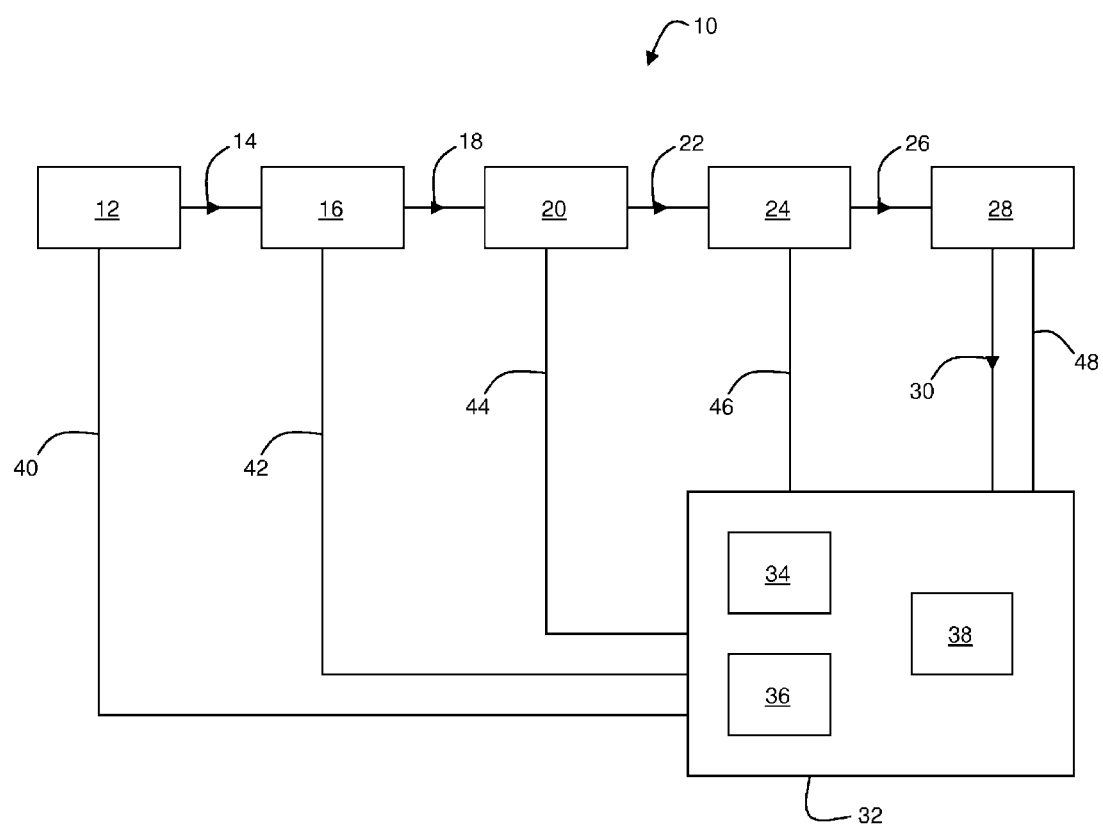
FIG. 1 is schematic diagram of a system for obtaining birefringence and non-birefringence images of a sample.

The inventors have recognized that valuable information can be obtained from both birefringence and non-birefringence images of stained tissue samples, and that combining birefringence images with non-birefringence images can be useful for visual assessments of stained samples. As disclosed herein, a stained sample is a sample into which one or more biological stains have been introduced, so that the stains are present within the sample. The biological stains can include absorptive stains and/or fluorescent stains, for example, and can be applied according to staining protocols. Alternatively, or in addition, the biological stains can include absorptive and/or fluorescent entities such as markers—absorptive and/or fluorescent chemical entities that can be introduced into the sample via genetic engineering and other techniques, for example. For the purposes of this disclosure, the term stained sample, except where explicitly noted otherwise, refers to a sample that has been modified to include one or more absorptive stains and/or markers, and/or one or more fluorescent stains and/or markers.

A birefringence image of a sample is one in which pixel values, which can be grayscale or color values, correspond, at least in part, to optical retardance at locations within the sample that correspond to the pixel positions. For example, a birefringence image can be a cross-sectional view of a sample measured in an object plane of an imaging system orthogonal to a propagation direction of illumination light. Each pixel value in the birefringence image can correspond to the retardance of the sample measured along the propagation direction, and in sample spatial regions that correspond to the pixel location.

A non-birefringence image of a sample is one in which image contrast is not significantly related to optical retardance and/or retardance orientation in the sample. In general, non-birefringence images can include images obtained by measuring absorption of incident light by a stained tissue sample, either in transmission mode (e.g., by measuring light transmitted through the sample) or in reflection mode (e.g., by measuring light reflected from the sample). Non-birefringence images can also include image obtained by measuring fluorescence of stained samples following irradiation of the samples with incident light. Non-birefringence images can include absorption images that correspond to relatively narrowband incident light (e.g., less than 10 nm), or to incident light having a broader bandwidth (e.g., tens to hundreds of nanometers). Similarly, non-birefringence images can include fluorescence images that correspond to relatively narrowband emission (e.g., less than 10 nm), or to emission having a broader bandwidth (e.g., tens to hundreds of nanometers).

In some embodiments, multiple non-birefringence images can be measured separately by using optical filtering techniques. In certain embodiments, multiple non-birefringence images can be measured at the same time via detectors that are sensitive to spectrally distinct wavelength channels. For example, certain CCD detectors are sensitive to red, green, and blue wavelength channels, and can be used to measure three non-birefringence images at the same time, one in each color channel. Composite images can also be generated by combining information from multiple non-birefringence (e.g., absorption and/or fluorescence) images.

As disclosed herein, an absorption image of a sample is an image in which contrast (e.g., variations in image intensity) are related substantially to attenuation of detected radiation due to absorption of a portion of the radiation by one or more absorptive chemical moieties present within the sample. A fluorescence image of a sample is an image in which contrast (e.g., variations in image intensity) are related substantially to emission of radiation by one or more fluorescent chemical moieties present within the sample following irradiation of the sample.

To measure absorption images of stained samples, the samples are typically irradiated with light having a central wavelength at which one or more stains in the stained sample absorb relatively strongly. Accordingly, measurement of birefringence images of stained samples has heretofore been regarded as an unproductive enterprise for at least two reasons. First, absorption of incident light by stains in the samples occurs relatively strongly, so that only a relatively small amount of incident light is either reflected from or transmitted by the sample when birefringence images are measured. As a result, the signal-to-noise ratio in such images can be relatively poor due to the relatively small amount of light reaching the detector.

Second, depending upon the particular stain (or stains) applied to the sample, the bound stain(s) may exhibit anisotropic absorption strength (e.g., stronger absorption for incident light polarized in one direction relative to another direction). The anisotropic absorption behavior of the stained sample may produce false birefringence signal in birefringence images of the stained sample; that is, the birefringence imaging technique may presuppose that attenuation of incident light due to absorption in the stained sample is isotropic, and therefore that any observed variation in transmitted or reflected light intensity is due to variations in retardance in the sample. Correcting birefringence images for anisotropic absorption by the stained sample has thus far not been successfully achieved.

The inventors have developed systems and methods which enable both birefringence and absorption measurements (e.g., obtaining both birefringence and absorption images) to be performed on stained samples. By virtue of the methods and systems disclosed herein, both birefringence and absorption images can be measured using incident light of the same wavelength. The systems disclosed herein are sufficiently sensitive so that errors in birefringence images—including, for example, errors due to anisotropic absorption in stained samples—do not preclude the use of such images for visual assessments and/or classification. Furthermore, the inventors have discovered that by obtaining birefringence measurements using incident light having a central wavelength that is well separated from absorption maxima of the stains applied to the stained sample, effects due to anisotropic absorption can be significantly reduced.

Visual assessment of images of stained tissue samples depends, in part, on the presence of sufficient contrast in the images so that features of interest can be identified. Many tissue samples are stained with one or more non-specific stains—that is, one or more stains that do not preferentially bind to specific structures within a sample, and that do not preferentially enhance images of certain structures within the sample relative to images of other portions of the sample. Instead, images of samples stained with non-specific stains typically exhibit relatively uniform spatial contrast, and variations in image intensity result substantially from structural variations within the sample rather than the binding properties of the applied stain(s).

In contrast, a specific stain is a stain that typically binds with significantly greater affinity to certain structures within a sample than to other structures within the sample, and/or enhances images of certain structures relative to images of other structures within the sample. Specific stains are typically applied to samples to enhance detection and/or imaging of particular structures of interest within the sample, especially in situations where the particular structures function as indicators for a disease condition or sample state.

Reasons for the use of non-specific stains are many. Typically, for example, non-specific stains are cheaper and faster to apply than specific stains. Often, a tissue sample is stained first with a non-specific stain and inspected under a microscope to identify certain structures and/or regions of interest. However, the application of the non-specific stain typically precludes the use of a specific stain on the same sample at a later time. For example, a non-specific stain such as H&E can be applied to a tissue sample and the sample can be examined under a microscope. If the presence of certain structural entities such as collagen fibers are detected or presumed based on the microscope examination, it would be desirable to apply a collagen-specific stain such as a trichrome stain or picosirius red to the tissue sample to more clearly delineate the fibers. However, the initial use of H&E can preclude the application of collagen-specific stains. Typically, a second tissue sample would have to be collected and stained with a collagen-specific stain.

The methods and systems disclosed herein enable both absorption and birefringence imaging of stained samples so that particular structures such as collagen can be readily identified and quantified even in samples that do not include specific (e.g., collagen-specific) stains. As a result, a single tissue sample can be used for both general imaging and examination, and in structure-specific visual assessment. This reduces both the costs of obtaining and processing samples, and the time required to complete assessments, and also ensures that all assessments are performed on the same sample.

The inventors have also recognized that information derived from both birefringence images and non-birefringence images (e.g., including absorption images and/or fluorescence images) of stained samples can be used to achieve accurate automated classification of the samples. In particular, classification based on information derived from both birefringence images and non-birefringence images can be more accurate than classification based on information derived from only one of these types of images.

In general, classification of images of stained tissue samples typically includes demarcating cells and/or structures of interest in the images from surrounding cells, structures, and interstitial tissue. Classification can include assignment of regions of a sample into multiple classes based on various criteria and/or information derived from one or more birefringence and/or non-birefringence images of the sample. The information can include, for example, spectral information (e.g., wavelength-dependent absorption and/or fluorescence information), texture information, topographical information, retardance magnitude and/or orientation information, and other information.

For example, in cancerous breast tissue samples, cancer cells can be classified and distinguished from different types of classified non-cancer cells such as stroma cells, epithelial cells lining ducts, and microphages. Some classification algorithms rely only on spatial information revealed through transmitted light images of the samples. The spatial information (e.g., textures, structures, sizes, spacings between components) can be revealed through contrast created by chemical interactions between the applied stains and components of the tissue samples, and also by the birefringence properties of the samples. The inventors have recognized that improved classification results can be obtained by combining information from both birefringence and non-birefringence images, and using the combined information as input information to a classifier that classifies images based on both types of information.

In addition, the inventors have recognized that it would be beneficial to generally provide imaging techniques that include the benefits of birefringence imaging (e.g., quantitative retardance information at a plurality of points within a sample image) and, at the same time, are generally applicable to samples that are stained with a variety of different stains. For example, the inventors have recognized that for identification of collagen and assessment of fibrosis, it would be beneficial (e.g., less costly and time-consuming) to assess collagen morphology in samples stained with more common, non-collagen-specific stains such as H&E, rather than with collagen-specific stains such as trichrome and picosirius red.

The present disclosure provides systems for obtaining both birefringence images and non-birefringence images of stained samples. The images can be combined to provide quantitative birefringence information about structures within the image such as collagen fibers. The birefringence information can be determined in an automated manner using algorithms implemented on a processor, and the processor can further be configured to provide an automated assessment of a condition such as fibrosis in a subject corresponding to the sample under study.

The images can also be combined to provide composite image data, which can then function as input to automated classification systems. Operating on the composite image data, the classification systems can produce improved classification of images of the stained sample. Quantitative information about the stained tissue samples (e.g., quantitative wavelength-dependent information, quantitative birefringence information) can be determined in an automated manner using algorithms implemented on an electronic processor, and the processor can further be configured to provide automated classification results.

Birefringence imaging relies on the manner in which polarized light interacts with a sample to provide information that is different from the information available in non-birefringence images. Tissue structures such as collagen and membranes include ordered molecules, which give rise to optical birefringence properties. When polarized light passes through a birefringent sample, the sample interacts with the polarized light to alter its phase. Typically, one component of the polarized light is temporally retarded to a larger extent than another, orthogonal component of the light. For example, where molecules in the tissue sample are ordered along a particular direction, the components of the polarized light that are oriented orthogonally with respect to the ordered direction can be retarded to a larger extent than components oriented parallel with respect to the ordered direction.

The methods and systems disclosed herein enable measurement of the retardation of polarized light through a sample on a pixel-by-pixel basis. The methods and systems permit measurement of two attributes of samples on a pixel-by-pixel basis: the magnitude of the retardation, in nanometers, and the orientation of the molecular order, in degrees in the plane of the image. In many embodiments, the birefringence images of the stained samples can be obtained even where the total birefringence (resulting from both the stain and inherent birefringence in the sample) is relatively small, for example, less than 200 nm (or less than 150 nm, or even less than 100 nm) for a tissue sample having a thickness as large as 10 microns. This is contrast to samples stained with substances such as picosirius red that artificially enhance the intrinsic birefringence of the sample to levels greater than, for example, 300 nm. Moreover, the retardance information in the birefringence image can be highly quantitative, with a resolution better than 10 nm, or better than 5 nm, or even better than 2 nm.

System Overview

FIG. 1 shows a system 10 configured to measure both birefringence images and non-birefringence images of a sample. System 10 includes a light source 12 that provides source light 14 to illumination optics 16. Illumination optics 16 transform source light 14 into illumination light 18, which is incident on stage 20. Stage 20 is configured to support a sample, and to position the sample with respect to illumination light 18. Detection optics 24 collect a portion of detection light 22 that emerges from the sample and direct the collected light 26 to a detector 28. Detector 28 measures light 26 and produces one or more electrical signals 30 corresponding to the measured light. Electronic control system 32 receives electrical signals 30. Electronic control system 32 includes a display 34, an interface 36 for receiving commands from a system operator, and a processor 38. Electronic control system 32 can exchange control and other signals with light source 12, illumination optics 16, stage 20, detection optics 24, and detector 28 via communication lines 40, 42, 44, 46, and 48, respectively.

Various polarization microscope systems can be used to obtain birefringence and non-birefringence images of samples. Suitable microscope systems are disclosed, for example, in U.S. Pat. No. 5,521,705 entitled "POLARIZED LIGHT MICROSCOPY" by Rudolf Oldenbourg et al., filed on May 12, 1994, and in U.S. Pat. No. 6,924,893 entitled "ENHANCING POLARIZED LIGHT MICROSCOPY" by Rudolf Oldenbourg et al., filed on May 12, 2003. The entire contents of each of these U.S. patents is incorporated herein by reference.

Figure 2:
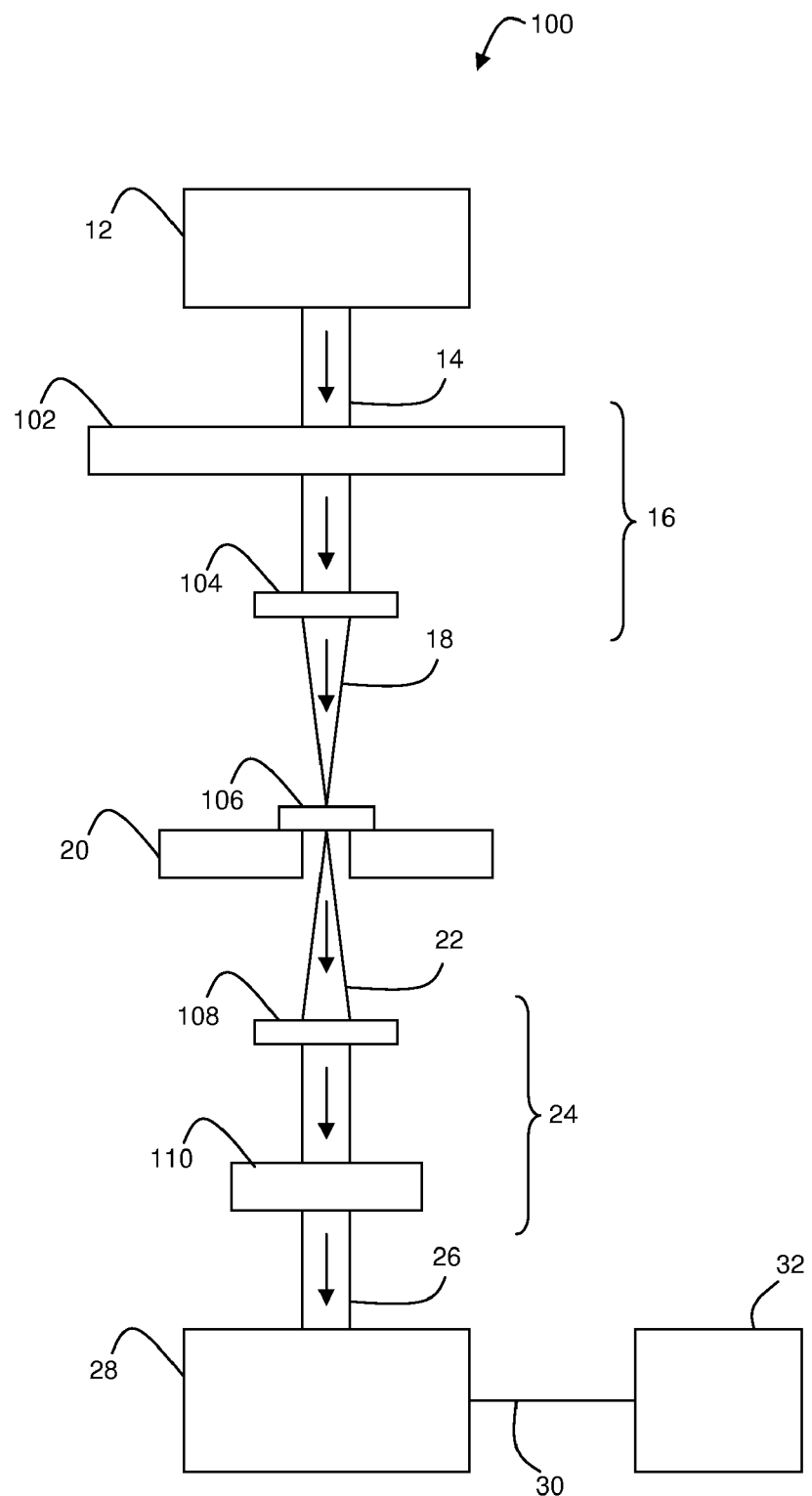
FIG. 2 is a schematic diagram of a microscope system for obtaining birefringence and non-birefringence images of a sample.

One embodiment of system 10 is shown in FIG. 2 as microscope 100. Microscope 100 includes light source 12 which directs source light 14 to illumination optics 16. Illumination optics 16 include polarization optics 102 and condenser lens 104. Polarization optics 102 are configured to manipulate the polarization properties of source light 14. For example, in some embodiments, polarization optics 102 can include a half-waveplate and a quarter-waveplate for generating circularly polarized illumination light 18. Either or both of the half-waveplate and the quarter-waveplate can be substantially achromatic, so that these elements function as a half-waveplate and a quarter-waveplate, respectively, over a relatively wide spectral bandwidth (e.g., over a spectral bandwidth that includes multiple wavelengths in source light 14). Condenser lens 104 directs circularly polarized illumination light 18 to sample 106.

In general, upon passing through sample 106, illumination light 18 becomes elliptically polarized due to birefringence in sample 106. Elliptically polarized detection light 22 is received by detection optics 24, which include an objective lens 108 and a tunable analyzer 110. Objective lens 108 collimates detection light 22 and directs the light to be incident upon tunable analyzer 110. Tunable analyzer 110 is configured to transform detection light 22. In some embodiments, for example, tunable analyzer 110 can be configured to reduce the intensity of detection light 22 in spatial regions of the light beam profile according to the retardance of sample 106 in corresponding spatial regions. In general, after passing through detection optics 24, light 26 has a cross-sectional intensity profile that provides quantitative spatially-resolved information related to spatially-varying retardance in sample 106. Light 26 is detected by detector 28 and electronic signals from detector 28 which correspond to optical retardance measurements of sample 106 are processed by electronic control system 32.

Measurement of Sample Images

Figure 3:
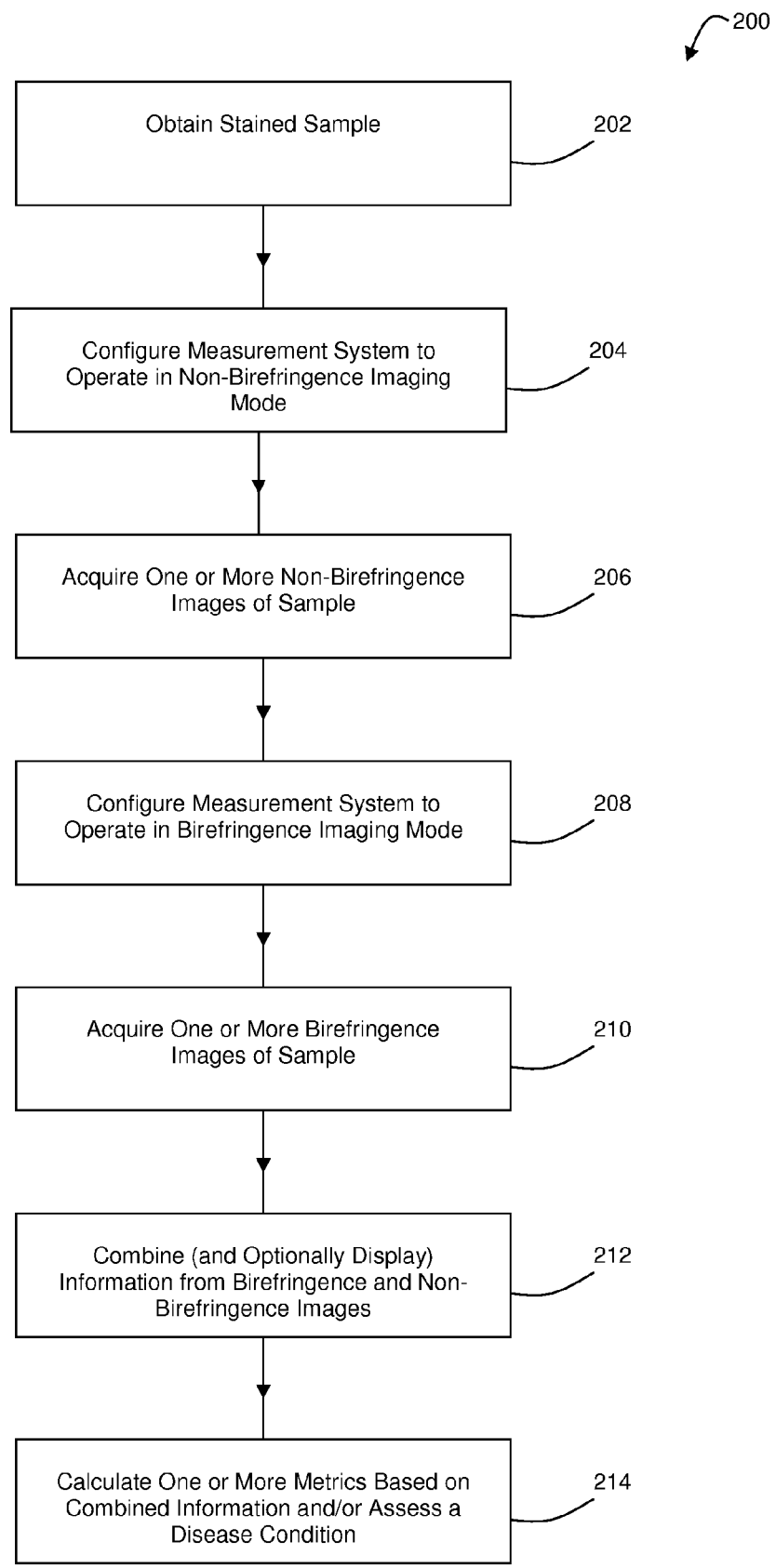
FIG. 3 is a flow chart showing a series of steps for determining one or more quantitative metrics from a stained sample.

In some embodiments, system 10 can be used to obtain both non-birefringence and birefringence images of a sample, and to calculate one or more metrics based on the images obtained. FIG. 3 is a flow chart 200 that shows a series of steps for obtaining sample images and calculating metrics. In a first step 202, a stained sample is obtained and mounted on stage 20. The sample can be a tissue section from a human or animal subject, for example. Samples can be stained with a variety of different biological stains (including more than one stain) such as H&E, for example.

Once the sample is affixed to stage 20 and positioned in the path of illumination light 18, system 10 is configured in step 204 to enter a non-birefringence imaging mode. For example, polarization optics 102 can be configured so that the polarization of source light entering illumination optics 16 is unchanged after emerging from illumination optics 16 as illumination light 18. Alternatively, in some embodiments, polarization optics 102 can be configured so that the polarization of illumination light 18 is linear (e.g., polarization optics 102 can be configured as a half-waveplate). Similarly, detection optics 24 are configured so that detection light 22 entering detection optics 24 after passing through sample 106 is not significantly modulated based on the birefringence of sample 106. For example, detection optics 24 can be configured to function as an isotropic window with no polarization-dependent attenuation of detection light 22. More generally, in the non-birefringence imaging mode, all polarization optics on one or both of the source and detection sides can be removed.

In step 206, one or more non-birefringence images (e.g., absorption images) of sample 106 are obtained with system 10 in the non-birefringence imaging mode configured in step 204. The non-birefringence images can be stored for further processing and/or can be combined according to an algorithm to emphasize particular image features, for example. In some embodiments, the non-birefringence images can be obtained with illumination light from multiple (e.g., three) different wavelength bands. Alternatively, multiple (e.g., three) different images of sample 106 can be obtained, each measured with illumination light from a different wavelength band. The multiple images can be combined to produce an image that corresponds to illumination with light from multiple different wavelength bands. An image produced with illumination light from three different wavelength bands can correspond to a red-green-blue (RGB) image, for example. More generally, complex spectral imaging techniques can be used on either the source or detection side to select certain spectral indices, some which may include more than three bands. Spectral imaging techniques are disclosed, for example, in the following commonly owned patents and patent applications: U.S. patent application Ser. No. 10/573,242 entitled "Spectral Imaging of Biological Samples," filed on Mar. 22, 2006; U.S. Pat. No. 6,690,466 entitled "SPECTRAL IMAGING SYSTEM"; and U.S. Pat. No. 6,825,930 entitled "MULTISPECTRAL IMAGING SYSTEM." The entire contents of each of the foregoing patents and patent applications are incorporated herein by reference.

After the non-birefringence images have been acquired, system 10 is configured in step 208 to operate in a birefringence imaging mode. Typically, sample 106 does not have to be translated or re-oriented as the imaging mode of system 10 is changed. In some embodiments, for example, polarization optics 102 are configured so that illumination light 18 that is directed to sample 106 is circularly polarized. Detection optics 24 are configured for polarization analysis (e.g., as a quarter-waveplate). The configuration of detection optics 24 imparts a modulation to detection light 22 that varies spatially according to the spatially varying birefringence of sample 106. Light 26 emerges from detection optics 24 after being modulated and is detected by detector 28.

In step 210, after system 10 has been configured to operate in birefringence imaging mode, one or more birefringence images of sample 106 are obtained. The birefringence images can be stored for further processing, and/or can be combined according to various mathematical algorithms. For example, in some embodiments, four different images of sample 106 are obtained, each with a different configuration of polarization optics 102. Each of the different images can be used to determine one component of optical retardance at each pixel in the image. Because no movement of sample 106 occurs between images, the four images are precisely registered with one another and with the one or more non-birefringence images recorded in step 206. Recording four different birefringence images for sample 106 permits calculation of both the magnitude and direction of light polarization within sample 106.

Next, in step, 212, information from one or more non-birefringence images and one or more birefringence images is combined. For example, in some embodiments, birefringence and non-birefringence images can be superimposed to produce a composite image. The combined birefringence and non-birefringence information provides a spatially resolved, quantitative measurement of birefringence in sample 106. For example, using the combined information provided by the birefringence and non-birefringence images obtained for sample 106, quantitative measurements of optical retardance variations in sample 106 of 200 nm or less (e.g., 150 nm or less, 100 nm or less, 80 nm or less, 70 nm or less, 60 nm or less, 50 nm or less, 40 nm or less, 30 nm or less, 20 nm or less, 10 nm or less) can be made. The combined information (e.g., in the form of one or more composite images) can be displayed to a system operator via display 34 as color-coded or grayscale images.

As an example, in some embodiments, a composite image can include an absorption image of the sample that is shaded in a first color (e.g., the color red), where an intensity of the first color at each pixel in the absorption image corresponds to a quantitative measurement of absorption by the sample in a region corresponding to each pixel. The composite image can also include a birefringence image of the sample that is shaded in a second color (e.g., the color blue), where an intensity of the second color at each pixel in the birefringence image corresponds to a quantitative measurement of retardance magnitude or orientation by the sample in a region corresponding to each pixel. The composite image is displayed to a system operator by overlaying the color-coded absorption and birefringence images. Overlap of color-coded areas in the two images are indicated in the displayed composite image by blending of the first and second colors. Similar overlay images can be produced by superimposing grayscale images of two or more planes of a composite image. In grayscale overlay images, corresponding highlighted regions of the images, when overlapped, can appear as either darker or lighter shades of grey. Alternatively, or in addition, shading patterns can be used to highlight features of planes in composite images; when the planes are overlaid, the shading patterns can blend to form new patterns that are not present in any of the individual planes of the composite image, thereby highlighting regions of the displayed composite image.

Finally, in optional step 214, one or more quantitative metrics can be calculated based on the combined birefringence and non-birefringence information. For example, in some embodiments, an algorithm can be applied to calculate optical retardance information from selected regions of one or more composite images. The regions can be selected manually by a system operator, or automatically via image processing algorithms. The optical retardance information can be used to calculate a metric based on the selected regions of the one or more composite images. In some embodiments, for example, the metric can be obtained automatically from a look-up table of optical retardance values. In other embodiments, the metric can be obtained via mathematical calculations according to one or more algorithms. Such algorithms can also take into account not only optical retardance values, but additional information as well (e.g., spatial derivatives of optical retardance, wavelength-dependent information).

The quantitative optical retardance information can be used to produce grayscale intensity maps of sample 106, where an intensity of each pixel is mapped to a quantitative measurement of optical retardance in a corresponding portion of sample 106. These grayscale maps can be displayed in place of, or in addition to, the overlay images on display 34.

Also in step 214, a disease condition in the sample (e.g., in a subject from whom the sample was derived) can be assessed based on the birefringence and non-birefringence information. One such disease that can be assessed is fibrosis, for which a useful indicator is collagen. In certain embodiments, step 214 can include first identifying the presence of collagen in the sample based on information derived from one or more birefringence images of the sample. Collagen fibers are particularly well-imaged in birefringence images, enabling either automatic (e.g., by an electronic processor equipped with a suitable search algorithm) or manual (e.g., by a system operator) identification. In addition to fibrosis, collagen fibers also function as indicators for a variety of other conditions. The systems and methods disclosed herein can also be used to assess these conditions.

To assess a particular type and/or stage of fibrosis—if collagen fibers are identified in the sample—a variety of information can be used. Metrics can be calculated based on information obtained from both birefringence and non-birefringence information, including retardance magnitude and/or orientation, the spatial extent of the collagen fibers, ordering of the fibers, density of the fibers, and other attributes of the fibers. Metrics based on this information can be assessed automatically by an electronic processor to determine fibrosis stage and/or type. For example, look-up tables that include references values of metrics can be consulted to assess fibrosis automatically. Alternatively, or in addition, metrics and/or visual information from the birefringence and/or non-birefringence images can be assessed by a system operator to determine fibrosis stage and/or type.

Figure 4:
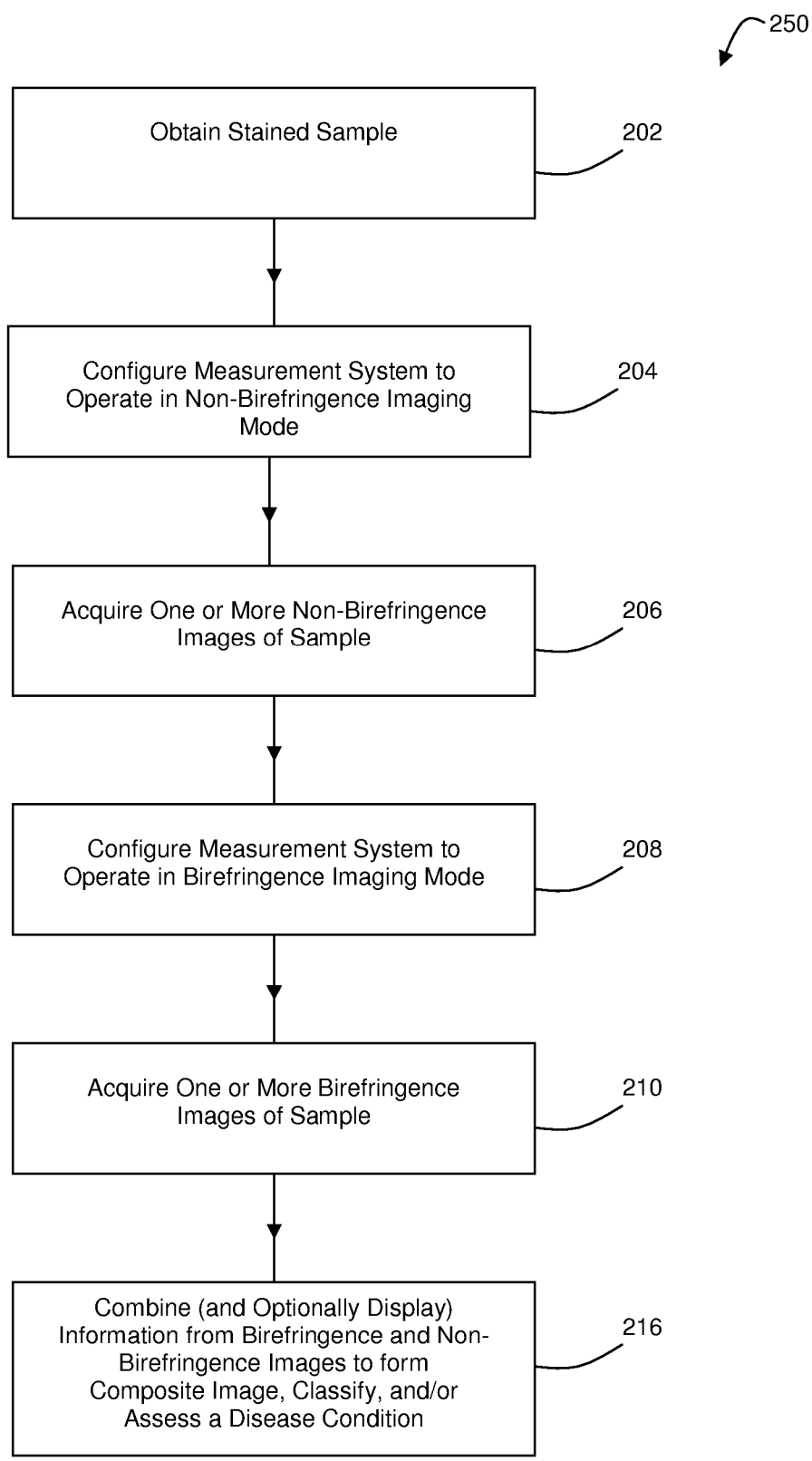
FIG. 4 is a flow chart showing a series of steps for obtaining images of a sample and classifying the images.

In some embodiments, information derived from birefringence and non-birefringence images of a sample can be combined, and the combined information can function as input information to an automated classifier than classifies regions of the sample based on the combined information. FIG. 4 shows a flow chart 250 that shows a series of steps for obtaining sample images and classifying a sample. Many of the steps in FIG. 4 are similar to those shown in FIG. 3, and the discussion of these steps will not be repeated.

However, as shown in FIG. 4, in the final step 216 in flow chart 250—after both birefringence and non-birefringence images of the sample have been obtained—information from one or more non-birefringence images and one or more birefringence images is combined to generate a composite image, and the composite image is classified. Typically, information (e.g., in the form of one or more composite or component images) can be displayed to a system operator via display 34 as color coded or grayscale images and/or maps, for example. In certain embodiments, the combined information can include quantitative data (e.g., birefringence magnitude and direction, topographic information), and this information can also be displayed to the operator graphically or as numeric data.

Step 216 can also optionally include assessing (e.g., automatically or manually) a disease condition in the sample based on information derived from the birefringence and/or non-birefringence images. Assessment of a disease condition in step 216 is similar to the assessment described above in connection with step 214 of FIG. 3.

Figure 5:
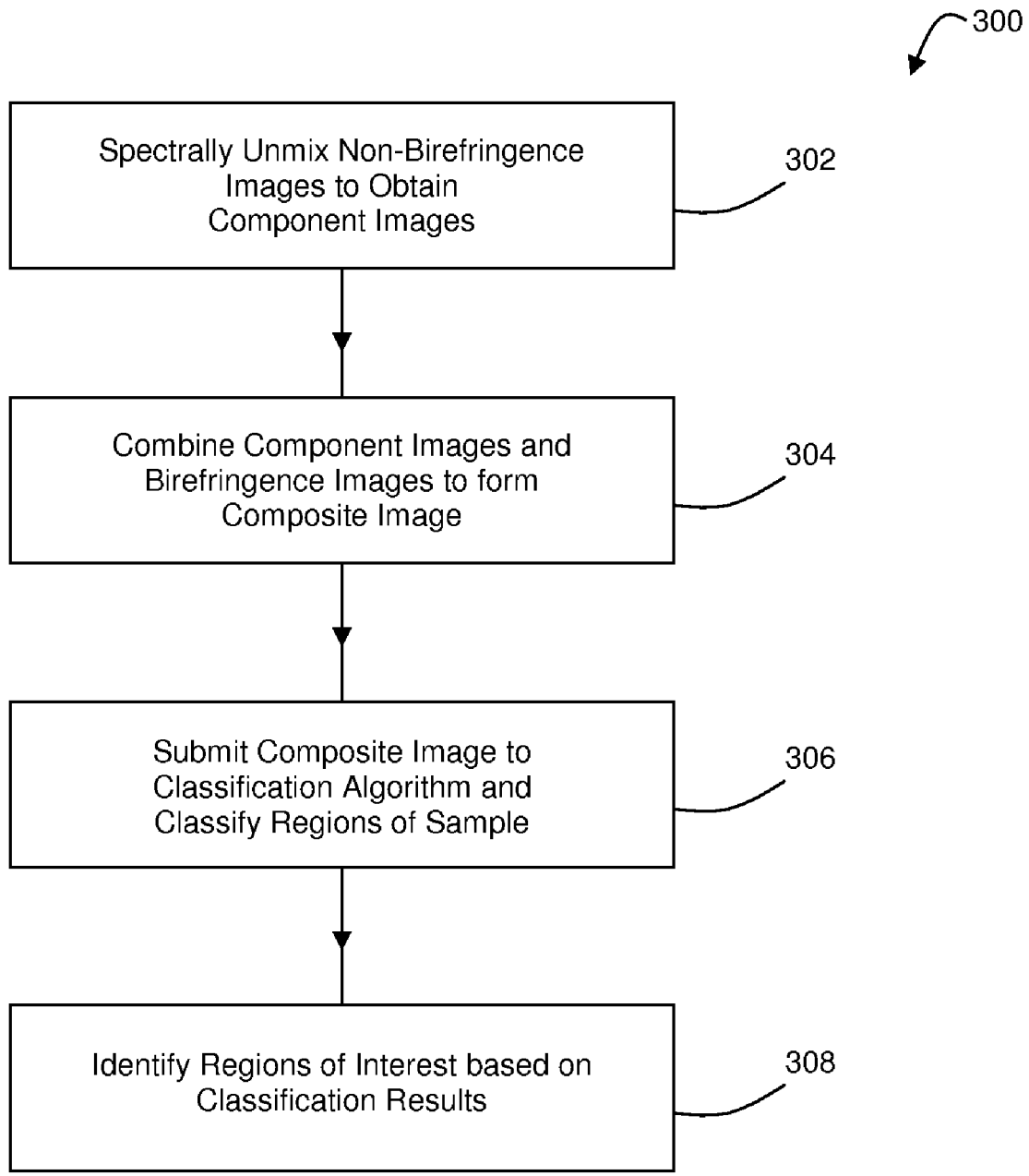
FIG. 5 is a flow chart showing a series of steps for generating and classifying a composite image of a sample.

The step of combining information to generate a composite image and then classifying the composite image involves multiple intermediate steps. FIG. 5 shows a flow chart 300 that includes several intermediate steps in the procedure. In a first step 302, one or more non-birefringence images of the sample are spectrally unmixed to obtain component images. As discussed above, one or more stains can be applied to the sample prior to obtaining sample images. Typically, at least some of the stains have absorption spectra that overlap spectrally, so that non-birefringence images of the stained sample include contributions from multiple stains. Spectral unmixing is a procedure whereby non-birefringence images (e.g., spectral images) can be decomposed into a series of images, each of which corresponds substantially only to contributions from a single spectral contributor such as a stain. The spectral unmixing procedure can be successfully performed even if the absorption spectra of some or all of the applied stains overlap significantly in the spectral domain. Spectral unmixing can also be performed on samples with only a single applied stain. Typically, biological samples exhibit natural autofluorescence that is due to tissues and structures in the sample, and is independent of any applied stains. Spectral unmixing can be used to separate tissue autofluorescence from spectral contributions to images of the sample that are due to applied stains. Methods and systems for spectral unmixing are generally disclosed, for example, in the following previously-referenced publications: U.S. patent application Ser. No. 10/669,101 entitled "SPECTRAL IMAGING OF DEEP TISSUE" by Richard Levenson et al., filed on Sep. 23, 2003, now published as U.S. Publication No. US 2005/0065440; PCT Patent Application No. PCT/US2004/031609 entitled "SPECTRAL IMAGING OF BIOLOGICAL SAMPLES" by Richard Levenson et al., filed on Sep. 23, 2004, now published as PCT Publication No. WO 2005/040769; and U.S. patent application Ser. No. 10/573,242 entitled "SPECTRAL IMAGING OF BIOLOGICAL SAMPLES" by Richard Levenson et al., filed on Mar. 22, 2006.

Spectral unmixing corresponds to a linear decomposition of an image or other data set into a series of components from different spectral contributors. Images of stained tissue sections typically include contributions from each of the individual stains applied to the tissue sections, and an autofluorescence contribution that arises from background fluorescence of the tissue. The contributions from the individual stains can include one or more contributions from immunohistochemical stains (e.g., brightfield contributions) and/or immunofluorescence stains/labels (e.g., darkfield contributions). Contributions to the stained tissue images can also arise from counterstains such as H&E. Each of these components can be unmixed or decomposed into a separate spectral channel, forming an image of the stained tissue section that corresponds almost entirely to signal contributions from only that component. When the components are unmixed into separate channels or images, signal strengths can be accurately quantified and analyzed.

The numerical spectral unmixing procedure will be described below for a tissue section that is stained with a single immunofluorescent (IF) label. The equations can be generalized in straightforward fashion to include spectral contributions from multiple IHC and/or IF stains. The spectral data recorded at a given point (x,y) in an image depends on the amount of fluorescence from the IF stain and on tissue autofluorescence as:

$$S(x,y,\lambda)=a(x,y)*F(\lambda)+b(x,y)*G(\lambda) \quad [1]$$

where (x, y) indices are used to denote a given pixel location in the image, the asterisk "*" denotes multiplication, λ is used to denote a given wavelength of fluorescence emission or detection, and S(x, y, λ) denotes the net signal for a given location and wavelength, F(λ) denotes the emission spectrum of autofluorescence, G(λ) denotes the emission spectrum of the IF stain, a(x, y) indicates the abundance of autofluorescence signal at a given (x, y) location, and b(x, y) indicates the abundance of IF stain fluorescence at a given (x, y) location.

Equation [1] states that the net signal from a given location is the sum of two contributions, weighted by the relative amount of autofluorescence and IF stain fluorescence present. It is easier to see if one writes the above equation for a single pixel:

$$S(\lambda)=a\,F(\lambda)+b\,G(\lambda) \quad [2]$$

F and G may be termed the spectral eigenstates for the system, which are combined in various amounts according to the amount of autofluorescence and IF stain emission, to produce an observed spectrum S.

Now if the emission spectra of the autofluorescence and of the IF stain are known (or can be deduced), one may invert equation [2] by linear algebra to solve for a and b, provided that the spectrum S has at least two elements in it, i.e., that one has data for at least two emission wavelengths λ. Then we can write $$A=E^{-1}S \quad [3]$$

where

A is a column vector with components a and b, and

E is the matrix whose columns are the spectral eigenstates, namely [F G].

Using equation [3], one can take the captured spectral images and calculate the abundance of the autofluorescence and of the IF stain sources. This process can be repeated for each pixel in the image, to produce separate images of the tissue section that correspond substantially to autofluorescence only, and to IF stain fluorescence only, and are free of contributions from other spectral sources. Note that the matrix E need only be inverted once for a given set of autofluorescence and IF stain spectra, so the calculation of abundances is not burdensome and can be readily done in nearly real-time by a personal computer.

In some embodiments, when multiple stains are applied to a tissue section, the individual spectra (e.g., the spectral eigenstates discussed above) of the stains are different than the spectra of the stains applied individually to tissue sections. These changes can arise, for example, from chemical interactions between the various stains, and/or from environmental conditions during or after the staining protocol. As long as these changes can be quantitatively reproduced in control experiments to provide accurate spectral eigenstates for the unmixing algorithm, however, the individual contributions of these stains to spectral images of the tissue section can be separated to obtain quantitative information about the absolute amount of each stain present in the tissue section.

Typically, when multiple stains are used in a staining protocol, the stains are selected so that they overlap as little as possible spectrally, which assists the unmixing algorithm in achieving an accurate decomposition. However, in some embodiments, stains can be employed which have overlapping spectral features. The unmixing algorithm can still accurately separate the contributions of the spectrally overlapped stains, provided the spectral eigenstates corresponding to the individual stains are known with relatively high accuracy.

The next step 304 in flow chart 300 includes combining one or more of the unmixed component images with one or more birefringence images to form a composite image. Images can be combined in various ways to generate the composite image. Typically, for example, birefringence and non-birefringence images are assembled to form two-dimensional arrays or planes in a three-dimensional image stack, where the composite image corresponds to the image stack. In some embodiments, the two-dimensional planes of the image stack can be formed by mathematical combinations of the unmixed spectral component images and birefringence images. For example, images can be added, subtracted, multiplied, or divided to generate planes of the composite image. Images can also be combined numerically, on a pixel-by-pixel basis, according to more complex mathematical formulas, such as linear and/or higher-order polynomial combinations. In general, any mathematical formula or algorithm can be used to combine images to generate planes of the composite image. The composite image functions as input to a classification algorithm, and any technique for combining images that produces a composite image that can be classified can generally be used in step 304.

Generally, composite images can include one or more non-birefringence images (e.g., absorption images and/or fluorescence images) of the sample, and one or more birefringence images of the sample. Each of these different types of images can form planes in the image stack that corresponds to the composite image. Absorption images, fluorescence images, and birefringence images can also be combined to form additional planes in the composite image. For example, multiple absorption images, multiple fluorescence images, and mixtures of absorption and fluorescence images can be combined to form additional planes. In addition, multiple birefringence images can be combined to form planes of composite images, and birefringence images can be combined with absorption images and/or fluorescence images to form composite image planes.

Typically, it can be desirable for tissue classification algorithms to be applied to images that correspond to stains that stain all cells of a particular type roughly equally (for example, all cancer cells in a tissue sample) regardless of the molecular state of the cells, so as to provide an accurate denominator for determining the extent to which the tissue exhibits a particular disease mechanism. If classification algorithms are applied to one or more stain(s) that are specific to a particular disease mechanism, the results of automated classification may not be as accurate. In general, counterstains stain substantially all cells in sample tissues, and as a result, classification algorithms typically work accurately on composite images that include at least one component (e.g., one plane) that corresponds to a counterstain applied to the sample. Counterstains can reveal important morphological information in the sample, and classification based, at least in part, on counterstain-based images provides results that are relatively robust across various tissue architectures and staining protocols.

In a typical procedure, prior to classification, a non-birefringence image of the sample is spectrally unmixed to obtain a series of component images, where each component image corresponds to a disease type-specific stain, to a counterstain, or to tissue autofluorescence. At least one of the component images that corresponds to a counterstain (e.g., hematoxylin) is then combined with one or more birefringence images of the sample to generate an image stack corresponding to the composite image. In some embodiments, for example, the image stack corresponding to the composite image includes three planes that correspond, respectively, to a counterstain-based image of the sample, a retardance-magnitude image of the sample, and a retardance-orientation image of the sample.

In some embodiments, the spectral images can be recorded at a small number of wavelength points, and spectral unmixing can still be performed accurately. For example, when a component image of interest (e.g., based on a counterstain) is substantially spectrally distinct from other component images, spectral images can be recorded at only three calorimetric red (R), green (G), and blue (B) wavelengths. Because these three wavelengths are well-separated spectrally, spectral unmixing can yield accurate results. When obtaining images of the sample, a conventional color (RGB) camera can be used in place of a spectral imaging device such as a spectrometer.

As discussed previously, although the disclosure herein focuses primarily on absorptive stains, fluorescent entities such as stains and/or markers can also generally be used in combination with, or in place of, absorptive stains. Fluorescent stains can be applied to samples via staining protocols. Fluorescent markers can be introduced into samples using chemical methods, for example, and/or using biological methods such as genetic engineering techniques. Combining information from birefringence images of the sample with information from non-birefringence images that correspond to either or both of absorptive stains and fluorescent stains and/or markers can improve the robustness and accuracy of classification results.

Step 306 in flow chart 300 includes submitting the composite image to a classification algorithm and classifying various regions of the sample based on the composite image. Various classification algorithms can be used for this purpose, including machine learning algorithms, neural networks, and support vector machines. In particular, neural-network based classification algorithms can be used to rapidly and accurately classify sample regions. Suitable algorithms, methods, and systems for neural network-based classification of sample regions are disclosed, for example, in U.S. patent application Ser. No. 11/342,272 entitled "CLASSIFYING IMAGE FEATURES" by Richard Levenson et al., filed on Jan. 27, 2006, now published as U.S. Publication No. US 2006/0245631, the entire contents of which are incorporated herein by reference.

Neural network-based analysis algorithms are typically trained prior to performing automated classification of composite images. In some embodiments, training can be performed with operator guidance using, for example, a spectral image corresponding substantially only to an applied counterstain (e.g., hematoxylin) to provide a training set for the neural network. Training based on spectral images that correspond to counterstains, for example, enables classification of image features on the basis of morphology rather than molecular phenotype, which can be important to avoid molecular bias. In certain embodiments, vectors determined from a training session can be stored and later re-used, so that the analysis algorithm does not have to be trained each time a new tissue section is analyzed.

The neural network-based algorithms can be trained to recognize various cell classes and tissue classes of interest in images of stained samples. Neural network-based algorithms can be trained to automatically identify normal and cancerous regions in a sample image, so that operator-based selection of regions-of-interest in sample images is not required.

For example, in some embodiments, neural network-based classification algorithms can be trained to differentiate between four different types of regions in breast tissue sections: cancerous, normal, stroma, and inflammation. Training can be extended over multiple examples, but typically, different training samples and algorithms are used for different tissue types and/or cancers.

Classification results are typically displayed (e.g., via display 34) to the system operator in the form of one or more images. Classes of features can be color-coded or commonly shaded, for example, to indicate sample regions that belong to the same class. In optional step 308 of flow chart 300, one or more regions of interest can be identified on the basis of the classification results. Regions of interest can be identified automatically by processor 38 according to criteria such as morphology, spatial shape, and texture. Alternatively, or in addition, regions of interest can be identified manually by the system operator.

Imaging Modalities

In some embodiments, birefringence of sample 106 can be recorded using moderately narrowband radiation. For example, light source 12, in response to control signals from electronic control system 32 transmitted along communication line 40, is typically configured to provide source light 14 at a distribution of wavelengths, where a central wavelength of the distribution is $\lambda$ and a full-width at half maximum bandwidth of the distribution is $\Delta\lambda$. Typically, $\lambda$ is in a visible region of the spectrum (e.g., $\lambda$ is between about 400 nm and about 800 nm), although $\lambda$ can also be in an ultraviolet region or an infrared region of the spectrum. The bandwidth $\Delta\lambda$ of the distribution is typically 100 nm or less (e.g., 80 nm or less, 70 nm or less, 60 nm or less, 50 nm or less, 40 nm or less, 30 nm or less, 20 nm or less, 10 nm or less, 5 nm or less, 1 nm or less, 0.5 nm or less, 0.1 nm or less). Bandwidths of 20 nm or less can be particularly useful in certain embodiments.

In some embodiments, when birefringence images of the sample are measured, the central wavelength $\lambda$ differs from a wavelength of maximum absorption, $\lambda_{max}$, of one of the stains used to stain sample 106 by 50 nm or more (e.g., by 60 nm or more, by 70 nm or more, by 100 nm or more, by 150 nm or more, by 200 nm or more, by 300 nm or more). Light source 12 can be configured to provide source light 14 in such a region to prevent significant absorption of source light 14 by certain stain molecules in sample 106, ensuring that an amount of illumination light 18 transmitted or reflected from sample 106 is relatively large.

However, the inventors have also discovered that high quality images and accurate quantitative retardance information can also be obtained, in some embodiments, where $\lambda$ and $\lambda_{max}$ differ by 30 nm or less (e.g., by 25 nm or less, by 20 nm or less, by 15 nm or less, by 10 nm or less, by 5 nm or less, by 1 nm or less, by 0.1 nm or less). Surprisingly, absorption of significant amounts of illumination light 18 by stain molecules in sample 106 does not preclude obtaining quantitative birefringence information from images captured under these conditions.

Microscope system 100 is configured to operate in transmission mode; that is, detection light 22 emerges from a side of sample 106 opposite the side upon which illumination light 18 is incident. However, in certain embodiments, microscope system 100 can be configured to operate in reflection mode. For example, microscope system 100 can be configured obtain images of sample 106 in an epi-illumination mode where detection light 22 retraces at least a portion of the path of illumination light 18. In these configurations, some optical elements can be common to both illumination optics 16 and detection optics 24. For example, one or more polarization manipulating optical elements can be configured both to condition the polarization of illumination light 18, and to analyze the polarization of detection light 22. In addition, one or more lens elements can be configured to both direct illumination light 18 to be incident on sample 106, and to collect reflected light from sample 106. In some embodiments, as shown in FIG. 2, detection light 22 corresponds to a portion of illumination light 18 that is either transmitted through sample 106 or reflected from sample 106.

Non-birefringence image(s) can be acquired in many ways, including by using the same or a different imaging system from the system used to acquire the birefringence image(s). Typically, acquiring non-birefringence image(s) involves making measurements at one or more (e.g., three) different wavelength bands. For example, the response of the sample (e.g., transmission, reflectance, fluorescence, and/or scattering) to excitation at different wavelength bands can be imaged to provide the non-birefringence image(s). In another example, the response of the sample to a broadband (e.g., white light) or narrow-band emission can be spectrally resolved into the one or more wavelength bands to provide the non-birefringence image(s). Thus, in some embodiments, the response of the sample (e.g., transmission or reflectance) to white light illumination can be measured at each of red, green, and blue spectral channels to provide a color image. This can be accomplished by using a color-CCD camera or a similar multi-channel spectral detector.

Optical and Electromechanical Systems

The optical and electromechanical elements used in the systems disclosed herein provide for configurable variation in functionality of the systems. Light source 12 can include a lamp, for example, such as an incandescent lamp, a halogen lamp, or a fluorescent lamp. Alternatively, light source 12 can include one or more light emitting diodes (LEDs). In some embodiments, light source 12 can include a laser source such as a continuous-wave laser or a pulsed laser. Multiple different light emitting elements can be included in light source 12 to provide source light 14 that has a distribution of wavelength components. Light source 12 can also include other elements such as passive and active filter elements for controlling the spectral distribution of source light 14. Active light filtering elements (e.g., liquid crystal-based optical filters) can include electronic devices such as power supplies and control modules for configuration. Any of the electronic components of light source 12 can be configured to receive and transmit electronic signals to electronic control system 32 via communication line 40.

Illumination optics 16 and detection optics 24 can include similar types of optical elements. For example, illumination optics 16 and detection optics 24 can include passive and/or active polarization-manipulating components such as liquid crystal modulators, crystal waveplates, electro-optic modulators, acousto-optic modulators, and other such components. Each of these components can receive and transmit control signals to electronic control system 32 via communication lines 42 and 46. Illumination optics 16 and detection optics 24 can also include optical elements such as lenses and mirrors for focusing, collimating, defocusing, and re-directing light. These elements can be passive or active, and can be controlled via signals transmitted along communication lines 42 and 46. Further, illumination optics 16 and detection optics 24 can include filter elements such as tunable liquid crystal bandpass filters. Tunable bandpass filters can be positioned in front of a circular polarizer in illumination optics 16 or following a polarization analyzer in detection optics 24, for example.

In some embodiments, certain components can perform multiple functions. For example, tunable filter 110 can function as both a tunable wavelength filter for obtaining non-birefringence images of a sample, and as a polarization analyzer for obtaining birefringence images of the sample. The polarization analyzer can be switched off during measurement of non-birefringence images, for example. Alternatively, the polarization analyzer and wavelength filter can separable components so that each component can be rotated out of the optical path when the other component is active.

In general, polarization optics 102 and tunable analyzer 110 are positioned on opposite sizes of sample 106. As shown in FIG. 2, polarization optics 102 can be positioned closer to source 12 than tunable analyzer 110. However, in certain embodiments, the ordering of the components can be reversed, and tunable analyzer 110 can be positioned closer to source 12.

Stage 20 provides mechanical support for sample 106, and can be translated independently along three orthogonal coordinate axes in response to control signals from electronic control system 32 to position sample 106 with respect to illumination light 18. In some embodiments, stage 20 also provides for rotation of sample 106 about one or more axes to orient sample 106 relative to the propagation direction of illumination light 18. The position and orientation of stage 20 can be changed via control signals from electronic control system 32 transmitted along communication line 44.

Detector 28 can include one or more CCD or CMOS detector arrays, for example, configured to measure an intensity of light 26 emerging from detection optics 24. Detector 28 can receive control signals from electronic control system 32 via communication line 48 to control the timing and duration of exposure and other aspects of the detector's operation. Image data, encoded as electronic signals 30, can also be transmitted to electronic control system 32 via communication line 48.

Electronic control system 32 includes display 34 for displaying images and other data to a system operator, interface 36 for accepting input and commands from the operator, and processor 38 to carry out various data processing an instrument control steps.

Many variations of the components for acquiring the images are possible.

For example, detector 28 can include a monochrome light sensor, used in concert with suitable illumination light (including, in some embodiments, one or more filters used to condition the illumination light) to obtain non-birefringence images at one or more colors. In some embodiments, when a singly-stained sample is imaged, a single filter or illumination setting may suffice, and in some embodiments the same filter or illumination setting can be used for birefringence imaging as well as for non-birefringence imaging of the sample.

Red-green-blue (RGB) cameras can also be used to obtain the non-birefringence images. RGB cameras typically provide a real-time RGB output signal that can be used for live sample viewing. When birefringence imaging is performed, the imaging system can be configured so that only a narrow wavelength band of light reaches the detector, so that one or more of the color channels are relatively inactive, and only one or two color channels provide useful signals for producing the birefringence images. Some camera sensors perform color interpolation as part of their normal action; defeating this interpolation can be beneficial to get relatively high signal fidelity in birefringence images. RGB cameras can use a single mosaic-type imaging sensor or multiple imaging sensors together with one or more dichroic elements.

In certain embodiments, a monochrome camera and an RGB camera can be combined in a single system. For example, the monochrome camera can be used for birefringence imaging, while the RGB camera can be used for non-birefringence imaging. Dichroic or partially reflective optical elements can be used to isolate spectral regions from one another during non-birefringence imaging. In some embodiments, it may be preferable to position dichroic beamsplitting elements after the polarization analyzer to avoid introducing wavelength-dependent polarization effects in the beamsplitter.

Illumination sources can include lamps, LEDs, and other sources. It can be advantageous in some embodiments to use LEDs where these provide a convenient technique for obtaining RGB color images via sequential illumination; one of these LEDs, or another LED, can also be used as a birefringence imaging light source. This can permit easy adjustment of illumination characteristics (e.g., brightness, wavelength) during the image acquisition sequence. In general, any optical element that provides the desired wavelength(s) can be used.

In some embodiments, the polarizer and/or the analyzer can be electrically switchable. For example, when liquid crystal elements are used for the waveplate elements, their retardance can be electrically variable. This can provide a convenient way to achieve a nearly isotropic state. For example, by adjusting the switchable element so that the analyzer transmits nearly all the light, an image is produced where the image intensity is only weakly dependent on sample retardance. This method can be used to acquire non-birefringence images. Properties of the other polarizer element do not have to be altered.

Birefringence images are sometimes acquired using more than four polarized-light images. Methods for acquiring birefringence images using two, three, four, and five images are disclosed, for example, in Shribak and Oldenbourg, "Techniques for fast and sensitive measurements of two dimensional birefringence distributions", Applied Optics 42(16): 3009 (2003), the entire contents of which are incorporated herein by reference. These or other methods can be used as long as they produce birefringence images of suitable resolution to detect structures of interest in the samples.

In general, one can acquire the non-birefringence images and the birefringence images in any order. For example, in the flow charts shown in FIGS. 3 and 4, non-birefringence images are acquired first, followed by acquisition of birefringence images. Generally, however, either type of image can be acquired first, and then the system can be reconfigured to acquire the other type of image.

Electronic Processing and Software

Automated methods for configuring optical and electronic components of the systems described herein, and methods for collecting, processing, analyzing, interpreting, and displaying information (e.g., birefringence and non-birefringence information) from samples can be performed by electronic processors (such as computers or preprogrammed integrated circuits) executing programs based on standard programming techniques. Such programs are designed to execute on programmable computers or specifically designed integrated circuits, each comprising a processor, a data storage system (including memory and/or storage elements), at least one input device, and at least one output device, such as a display or printer. The program code is applied to input data (e.g., image data from a detector) to perform functions and generate output information (e.g., birefringence and non-birefringence images of samples, quantitative optical retardance information, etc.), which is applied to one or more output devices. Each such computer program can be implemented in a high-level procedural or object-oriented programming language, or an assembly or machine language. Furthermore, the language can be a compiled or interpreted language. Each such computer program can be stored on a computer readable storage medium (e.g., CD-ROM or magnetic diskette) that, when read by a computer, can cause the processor in the computer to perform the analysis and control functions described herein.

EXAMPLES

The following examples are not intended to in any way limit the scope of the disclosure described in the claims.

The systems and methods disclosed herein can be used to examine many different samples. For example, one application of the systems and methods includes assessment of fibrosis in human and animal subjects. A tissue section from a human or animal subject can be stained with a biological stain such as H&E and can be examined using system 10. On the basis of quantitative birefringence and/or non-birefringence information obtained during this examination, an assessment of fibrosis can be made. For example, regions of the tissue section that correspond to collagen fibers can be selected manually by a system operator, or automatically according to a searching algorithm implemented by processor 38 based on information derived from one or more birefringence images of the tissue section. Optical retardance information (and other information) from the selected regions can be used to calculate one or more metrics. For example, the collagen fibers in selected regions of the sample can be classified as type I, type II, or type III collagen based on a look-up table that includes information such as ranges for particular metrics that correlated with different types of collagen. Information that can be included in a look-up table includes, for example, retardance magnitude and/or orientation, spatial extent of fibers, spatial ordering of fibers, fiber density, fiber texture, topographic information, and fiber aspect ratio. Thereafter, an assessment of fibrosis stage in the subject, based on the amount and type of collagen fibers present in the tissue section, can be made by a trained individual, or in automated fashion according to an algorithm implemented by processor 38.

Figure 6A:
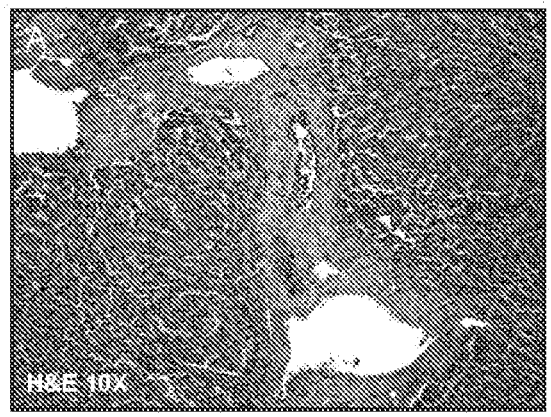
FIGS. 6A-D are images of a stained liver biopsy section under different imaging conditions.
Figure 6B:
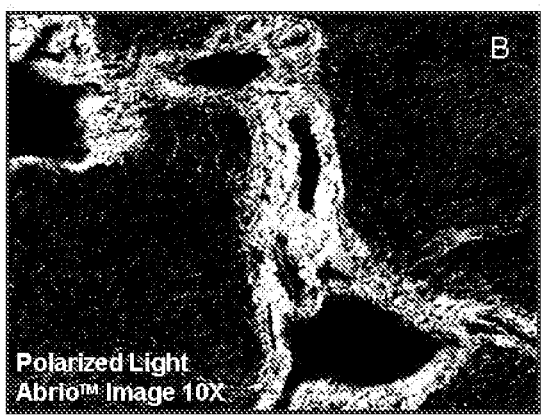
Figure 6C:
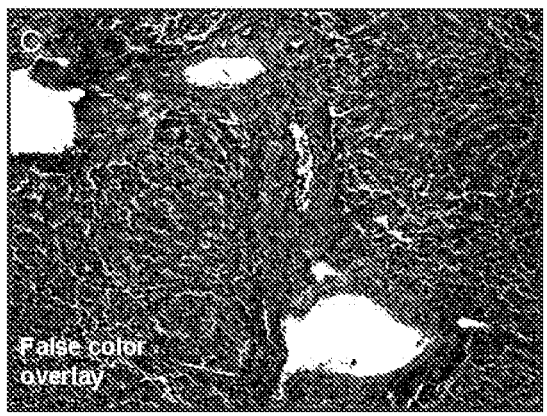
Figure 6D:
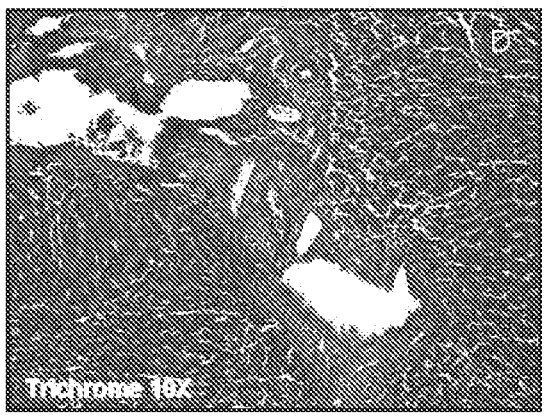

Examples of the results of measurements using a stained liver biopsy section are shown in FIGS. 6A-D. FIG. 6A shows a non-birefringence image of the H&E-stained sample at 10× magnification, and FIG. 6B shows a birefringence image of the same sample. Information from the images in FIGS. 6A and 6B is combined in FIG. 6C to produce a false color overlay image that includes quantitative birefringence information. FIG. 6D shows an RGB (e.g., non-birefringence) image at 10× magnification of the same sample stained with trichrome. The image contrast and level of detail in FIG. 6C is considerably superior to the image contrast apparent in FIG. 6D. The image shown in FIG. 6C can subsequently be used for assessment of fibrosis in a subject, for example.

Figure 7A:
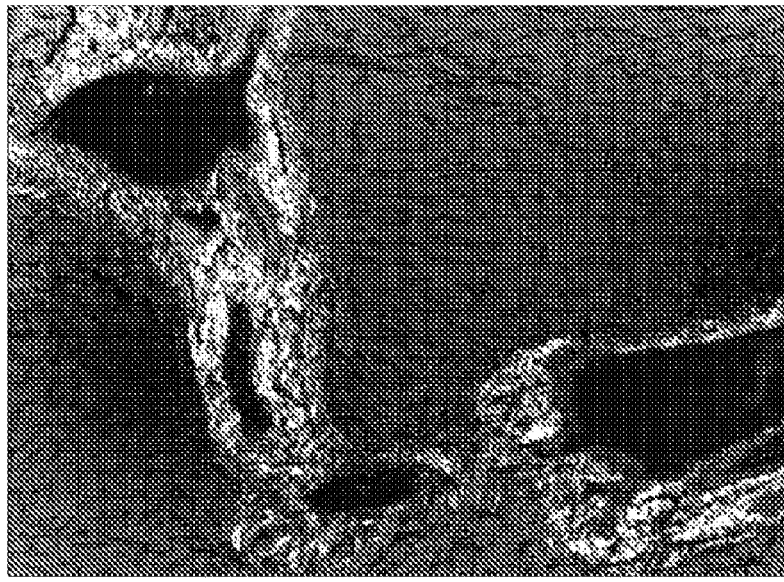
FIGS. 7A and 7B are birefringence images of a stained liver biopsy section measured at two different wavelengths.
Figure 7B:
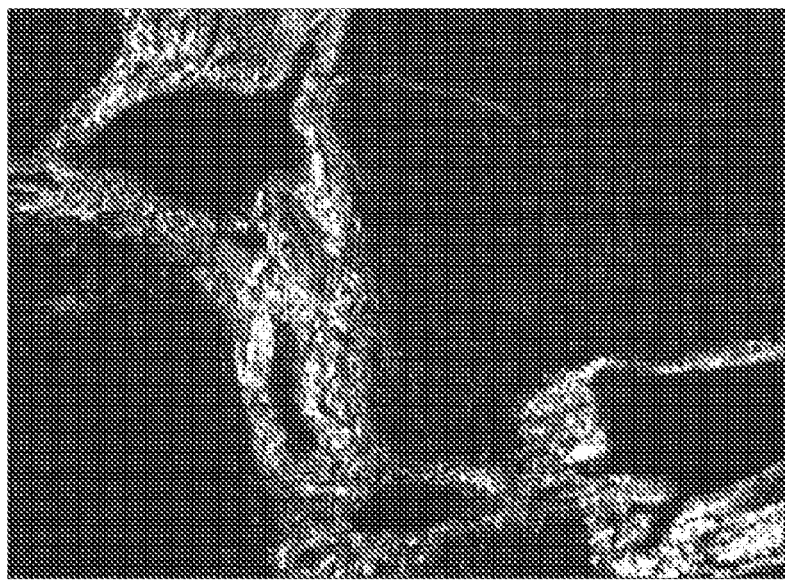

One advantage of the methods disclosed herein is that the results are relatively independent of the central wavelength λ of source light 14. For example, FIGS. 7A and 7B correspond to birefringence images of an H&E-stained liver biopsy section illuminated at 546 nm and 695 nm, respectively. Contrast in the images is similar, although certain features (e.g., features indicated by the arrows) appear brighter at one wavelength than at another.

Figure 8A:
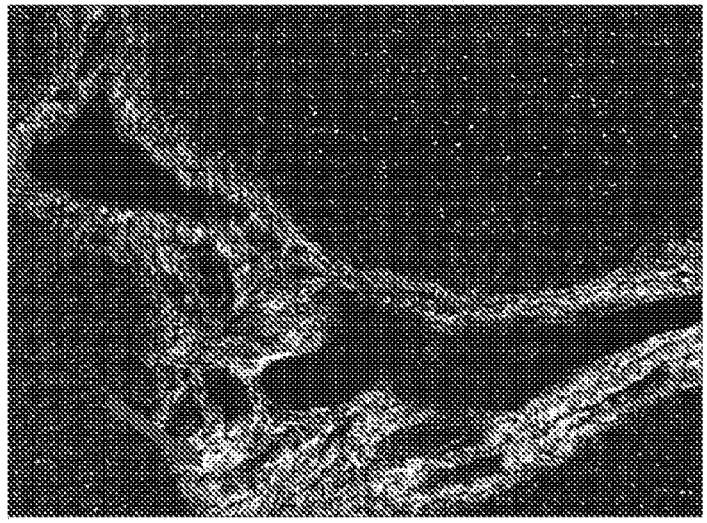
FIGS. 8A and 8B are birefringence images of an unstained liver biopsy section measured at two different wavelengths.
Figure 8B:
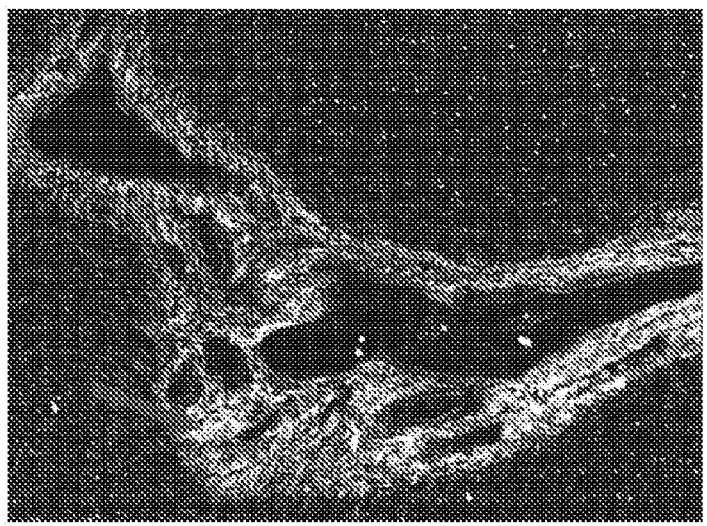

In some embodiments, it may not even be necessary to stain a sample to improve image contrast using the methods disclosed herein. For example, FIGS. 8A and 8B show two birefringence images of an unstained liver biopsy section illuminated at 546 nm and 695 nm, respectively. Image contrast and level of detail is similar in the two images, although certain features appear brighter in one image (e.g., at 695 nm) than in the other image (e.g., at 546 nm).

Quantitative birefringence imaging of stained samples can also be used in other applications. For example, birefringence imaging and specialized stains have been shown to be useful in surgical pathology for diagnosis of amyloid diseases. Amyloidosis is a heterogeneous clinical disorder caused by extracellular deposition of proteins that are normally soluble. In this condition, insoluble, abnormal fibrils can accumulate and impair organ function. Amyloid deposits may occur in many organs (systemic amyloidoses) or may affect a single tissue (localized or organ-specific amyloidoses). For the diagnosis of amyloidosis, histological evidence of amyloid deposition is essential. Histologically, an amyloid deposit is stained orange-red with Congo-red and exhibits green birefringence under polarized light (see, for example, the following references: Hoshii, Y., "Histopathological diagnosis of amyloidosis," Rinsho Byori 54(5): 513-518 (2006); Wolman, M., "Amyloid: Its nature and molecular structure. Comparison of a new toluidine blue polarized light method with traditional procedures," Lab. Invest. 25(2): 104-110 (1971); and Tashima, T. et al., "Congophilia in cerebral amyloidosis is modified by inactivation procedures on slow transmissible pathogens," Brain Res. 399(1): 80-86 (1986)).

Viewing samples stained with Congo-red on a conventional polarized light microscope, such as a microscope equipped with crossed or nearly crossed linear or circular polarizers, provides visual color cues which relate qualitatively to sample birefringence. However, precise and accurate quantitative measurements of birefringence in images of such samples is typically not possible. At best, visual characterization of birefringence levels into two or three coarse categories can be achieved.

Amyloid deposits and their resulting clinical manifestations originate from a diverse and heterogeneous group of proteins. More than 25 different fibril protein species have been identified to date with varying primary structure and function (see, for example, Rocken, C. and Sletten, K., "Amyloid in surgical pathology," Virchows Arch. 443(1): 3-16 (2003)). The only common denominator is the propensity to form a characteristic spatial structure of beta-sheet fibrils assembled into highly ordered bundles which results in a pathognomonic red-green birefringence when viewed under cross-polarized light after staining with Congo red (see, for example, the following references: Wolman, M., cited above; Tashima, T. et al., cited above; Linder, E., Lehto, V. P., and Virtanen, I., "Amyloid-like green birefringence in cytoskeletal 10 nm filaments after staining with Congo red," Acta Pathol. Microbiol. Scand. A 87A(5): 299-306 (1979); and Defigueiredo, R. J. et al., "Color image analysis in neuroanatomical research: application to senile plaque subtype quantification in Alzheimer's disease," Neurobiol. Aging 16(2): 211-223 (1995)).

Congo red is a stain similar to picrosirius red in that it enhances the natural birefringence of extracellular structural proteins several-fold, to enhance retardances so that conventional polarized light microscopes yield discernable color signals and can be interpreted by eye.

Detection and characterization of amyloid is essential, since amyloid is treatable and different treatment regimens are applied to different amyloid diseases. Immunohistochemical examination of amyloid in formalin-fixed, paraffin-embedded sections is the standard method for clinical amyloid diagnosis of cerebrospinal amyloid plaques as in Alzheimer's disease, Kuru, Gerstmann-Straussler-Scheinker disease (GSS), sporadic Creutzfeldt-Jakob disease (sCJD) and variant Creutzfeldt-Jakob (vCJD) (see, for example, the following references: Liberski, P. P., "Amyloid plaques in transmissible spongiform encephalopathies (prion diseases)," Folia Neuropathol. 42 Suppl. B: 109-119 (2004); Moroncini, G. et al., "Pathologic prion protein is specifically recognized in situ by a novel PrP conformational antibody," Neurobiol. Dis. 23(3): 717-724 (2006); and Trifilo, M. J. et al., "Prion-induced amyloid heart disease with high blood infectivity in transgenic mice," Science 313(5783): 94-97 (2006).

Birefringence images of tissue samples that include extracellular structural proteins characteristic of amyloid deposits can be obtained without the use of exotic, specific stains such as Congo red. To the contrary, using the systems and methods disclosed herein, birefringence images can be obtained with more conventional non-specific stains that provide color contrast for initial visualization, or even without any stains at all. Information derived from such birefringence images can be used to help diagnose the different conditions described above.

Quantitative polarized light microscopy and birefringence imaging, as disclosed herein, can also be used in other applications by eliminating the need for specific histological stains used to identify and diagnose highly ordered infectious organisms such as fungi. For example, broad-spectrum fungal histochemical stains such as Gomori methenamine silver and the periodic acid-Schiff (PAS) stain are widely used but are less useful for selective staining and fungal typing than more specific stains. Congo-red staining and polarized light microscopy have been shown to be a useful stain for certain pathogenic yeast forms of Blastomyces and spherules of Coccidioides, and may be helpful for detecting certain infections and infestations by other organisms that might not be apparent with conventional H&E stains (see, for example, Lazcano, O. et al., "Combined histochemical stains in the differential diagnosis of Cryptococcus neoformans," Mod. Pathol. 6(1): 80-84 (1993)). On the other hand, using the quantitative birefringence imaging systems and methods disclosed herein, birefringence images of samples that do not include Congo red or other specific stains can be obtained, for example, even with conventional H&E staining or no stain at all. The images can then be used to identify various fungal types present in the samples.

Figure 9:
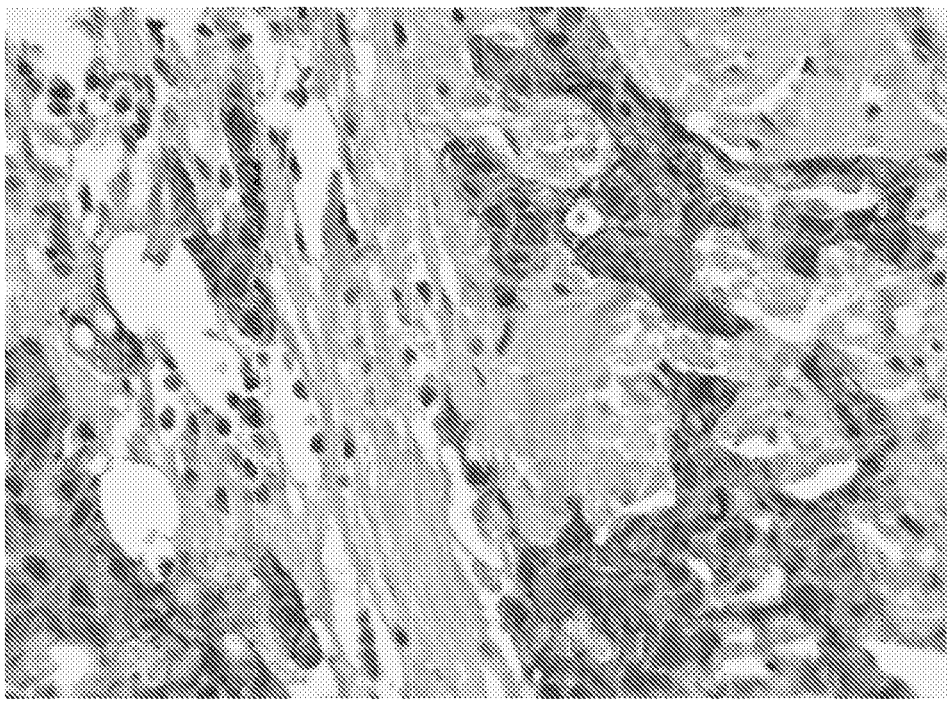
FIG. 9 is an image of a tissue sample stained with an immunohistochemical specific stain and a non-specific counterstain.

Another application of the systems and methods disclosed herein involves automated classification of cancer cells in tissue biopsy sections. FIG. 7 shows a non-birefringence image of a breast cancer tissue section stained with the specific stain Her2 new DAB, and with the counterstain hematoxylin. The image of FIG. 9 was spectrally unmixed to separate spectral contributors from one another, and FIG. 10 shows an image of the sample, obtained from the unmixing step, that corresponds substantially only to contributions from the non-specific hematoxylin counterstain.

Figure 11:
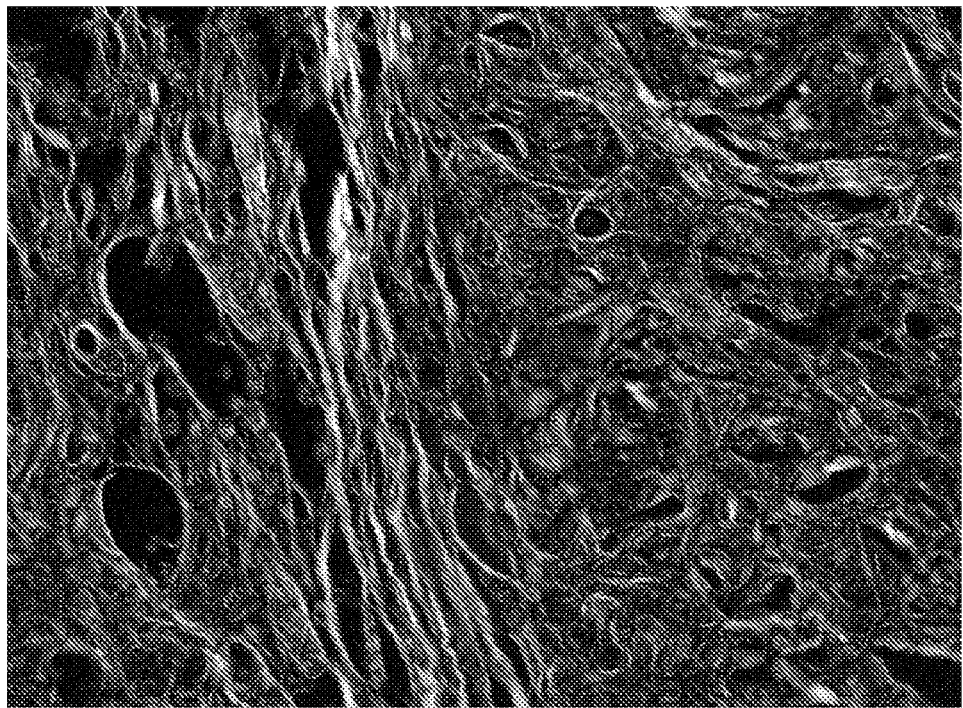
FIG. 11 is an image of the tissue sample of FIG. 9 that shows a magnitude of birefringence in the tissue sample.
Figure 12:
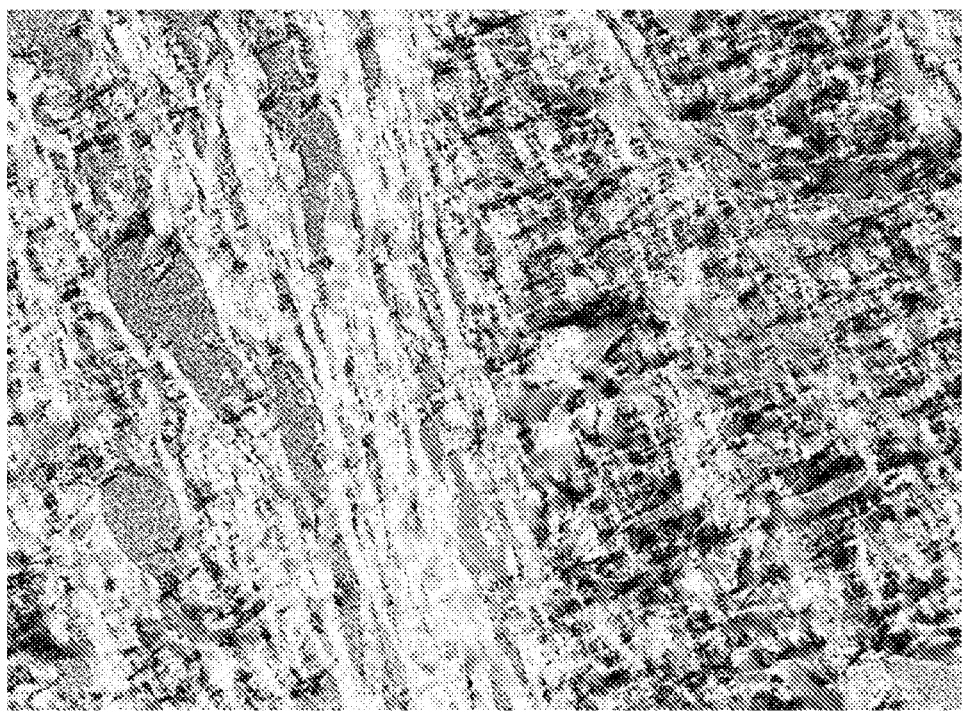
FIG. 12 is an image of the tissue sample of FIG. 9 that shows an orientation of birefringence in the tissue sample.

Following re-configuration of the imaging system to operate in birefringence imaging mode, birefringence images of the same tissue section were obtained and analyzed. FIG. 11 shows an image of the same tissue section where the grey level in the image corresponds to retardance magnitude in the tissue. FIG. 12 shows an image of the tissue section where the grey level in the image corresponds to retardance orientation direction in the tissue. These images were obtained following automated processing of the birefringence images of the tissue. Each of the images in FIGS. 9-12 is pixelwise registered to the other images because the sample was not moved when the imaging system was configured to operate in either birefringence imaging mode or non-birefringence imaging mode.

Figure 10:
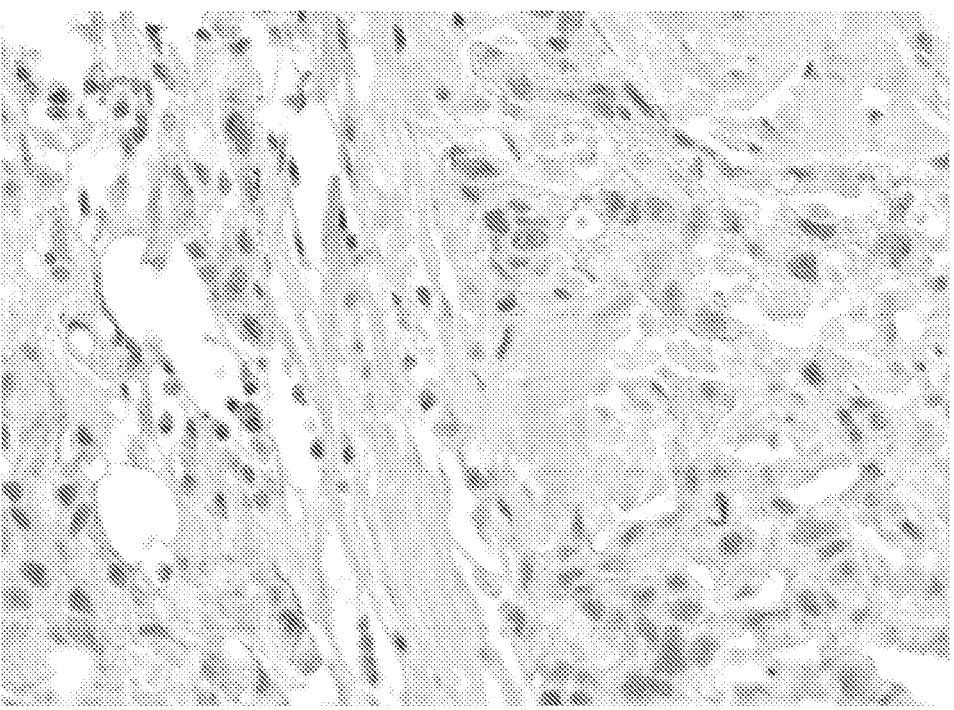
FIG. 10 is an image of the tissue sample of FIG. 9 that includes contributions from substantially only the counterstain.
Figure 13:
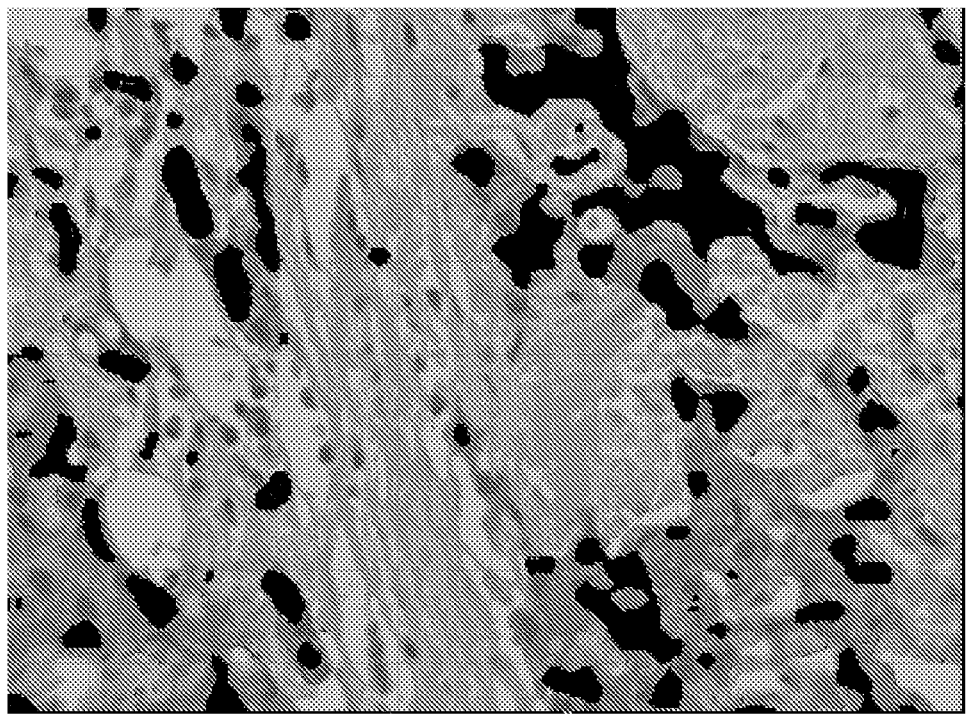
FIG. 13 is an image showing the results of a classification algorithm applied to the image of FIG. 10.

To demonstrate the improved classification results that can be obtained by combining birefringence and non-birefringence information, the image of the sample that includes contributions from substantially only the hematoxylin counterstain, shown in FIG. 10, was first classified using a neural network-based classifier. The classification results are shown in FIG. 13. The highlighted areas of the image in FIG. 13 correspond to cancer cells identified by the classification algorithm.

Figure 14:
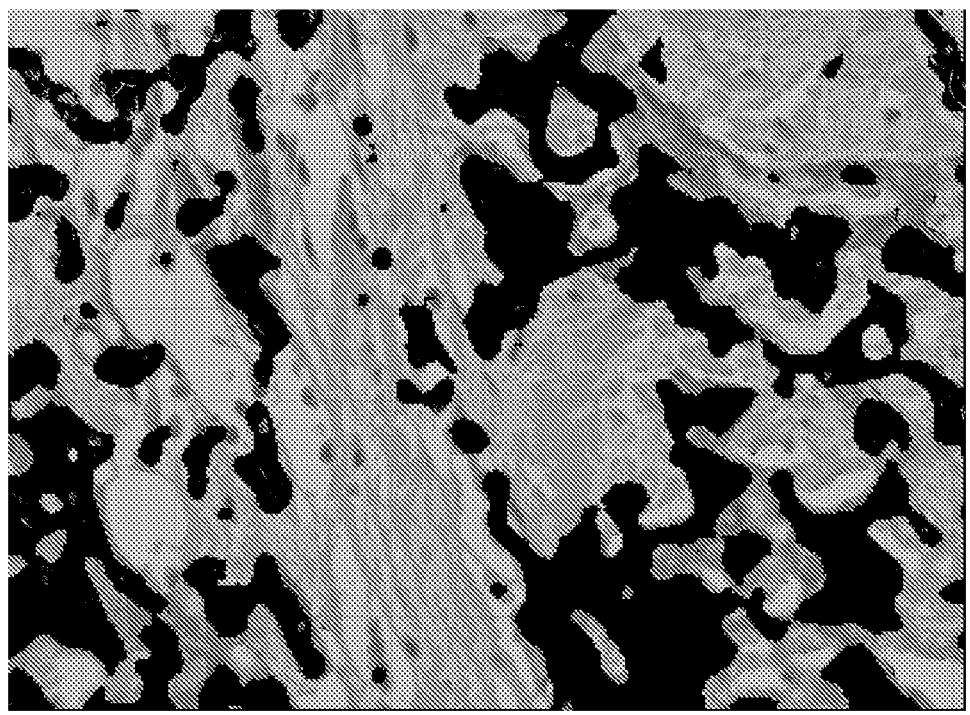
FIG. 14 is an image showing the results of a classification algorithm applied to a composite image formed by combining information from FIGS. 10-12.

Then, a composite image in the form of an image stack consisting of the images in FIGS. 10, 11, and 12 was constructed. The composite image was submitted to the neural network-based classifier. The classification results are shown in FIG. 14. The image in FIG. 14 shows that a significantly larger number of cancer cells (black regions) were identified by the classification algorithm operating on the composite image that included both birefringence and non-birefringence information. Similarly improved classification results are generally obtained when the methods and systems disclosed herein are applied to a wide variety of biological samples.

OTHER EMBODIMENTS

A number of embodiments have been described. Nevertheless, it will be understood that various modifications may be made without departing from the spirit and scope of the disclosure. Accordingly, other embodiments are within the scope of the following claims.

What is claimed is:

1. A method, comprising:
   obtaining at least one absorption image and at least one birefringence image of a stained sample; and
   using one or more processors, combining image information derived from the at least one absorption image and image information derived from the at least one birefringence image into a combined image, and assessing a disease condition in the stained sample based on the combined image.

2. The method of claim 1, wherein assessing a disease condition comprises assessing a type or a stage of fibrosis in the sample.

3. The method of claim 1, further comprising identifying the presence of collagen in the sample based on the at least one birefringence image.

4. The method of claim 3, further comprising assessing a disease condition in the sample based on the identified collagen.

5. The method of claim 3, wherein the at least one absorption image is obtained by measuring light absorption by one or more stains in the sample that are not specific for collagen.

6. The method of claim 5, wherein the measured light absorption does not arise from absorption of incident light by a trichrome stain, picosirius red, or Congo red.

7. The method of claim 3, wherein identifying the presence of collagen further comprises identifying one or more different types of collagen in the sample.

8. The method of claim 7, wherein the one or more different types of collagen are identified based on a comparison between birefringence information derived from the at least one birefringence image and a look-up table that comprises birefringence information.

9. The method of claim 1, wherein the at least one absorption image is obtained by directing light having a central wavelength that corresponds to a first wavelength to be incident on the sample, the at least one birefringence image is obtained by directing light having a central wavelength that corresponds to a second wavelength to be incident on the sample, and a difference between the first and second wavelengths is 5 nm or less.

10. The method of claim 1, wherein the at least one absorption image is obtained by directing light having a central wavelength that corresponds to a first wavelength to be incident on the sample, the at least one birefringence image is obtained by directing light having a central wavelength that corresponds to a second wavelength to be incident on the sample, and a difference between the first and second wavelengths is 50 nm or more.

11. The method of claim 1, wherein the sample comprises at least one fluorescent stain.

12. The method of claim 1, wherein the combined image can be represented as an image stack, wherein at least one plane of the image stack comprises information derived from an absorption image of the sample and at least one plane of the image stack comprises information derived from a birefringence image of the sample.

13. The method of claim 1, wherein the combined image comprises a composite image, and the method further comprises displaying the composite image to a system operator.

14. The method of claim 13, wherein the combining and displaying comprises producing a first color image of the sample based on an absorption image, producing a second color image of the sample based on a birefringence image, and overlaying the first and second color images to produce the composite image.

15. The method of claim 1, wherein obtaining at least one absorption image comprises obtaining two or more absorption images, and wherein each absorption image is obtained with incident light having a different central wavelength.

16. The method of claim 1, wherein obtaining at least one birefringence image comprises obtaining at least two birefringence images, and wherein at least one of the at least two birefringence images comprises information about a magnitude of optical retardance in the sample and at least one of the at least two birefringence images comprises direction information about optical retardance in the sample.

17. An apparatus, comprising:
a microscope imaging system configured to obtain at least one absorption image and at least one birefringence image of a stained sample; and
an electronic processor coupled to the microscope imaging system and configured to receive information about one or more stains in the stained sample, to combine image information from the at least one absorption image and image information derived from the at least one birefringence image into a combined image, and to identify structural entities in the sample based on at least a portion of the combined image.

18. The apparatus of claim 17, wherein the combined image can be represented as an image stack, and wherein at least one plane of the image stack comprises information derived from an absorption image of the sample and at least one plane of the image stack comprises information derived from a birefringence image of the sample.

19. The apparatus of claim 17, wherein the microscope imaging system is configured to obtain the at least one absorption image by measuring light absorption by one or more stains present in the sample that are not specific for collagen.

20. The apparatus of claim 17, wherein the structural entities comprise collagen.

21. The apparatus of claim 17, wherein the processor is configured to assess a disease condition in the sample based on the combined image.

22. The apparatus of claim 17, further comprising a display unit, wherein the combined image comprises a composite image, and wherein the processor is configured to display the composite image to a system operator.

23. The apparatus of claim 22, wherein the processor is configured to form the composite image by producing a first color image derived from the at least one absorption image, producing a second color image derived from the at least one birefringence image, and overlaying the first and second color images to form the composite image.

24. A method, comprising:
identifying collagen in a stained tissue sample, wherein the identifying comprises obtaining at least one absorption image of the sample by measuring light absorption by one or more stains in the sample that are not specific for collagen, obtaining at least one birefringence image of the sample, and, using one or more processors, combining image information derived from the at least one absorption image and image information derived from the at least one birefringence image into a combined image, and identifying collagen based on a portion of the combined image.

* * * * *

UNITED STATES PATENT AND TRADEMARK OFFICE
CERTIFICATE OF CORRECTION

| | | |
|---|---|---|
| PATENT NO. | : 8,126,205 B2 | Page 1 of 1 |
| APPLICATION NO. | : 11/861060 | |
| DATED | : February 28, 2012 | |
| INVENTOR(S) | : Richard Levenson and Clifford C. Hoyt | |

It is certified that error appears in the above-identified patent and that said Letters Patent is hereby corrected as shown below:

<u>Column 26</u>
Line 49, delete "picosirius" and insert -- picrosirius --

Signed and Sealed this
First Day of May, 2012

David J. Kappos
*Director of the United States Patent and Trademark Office*